United States Patent [19]

Mikayama et al.

[11] Patent Number: 5,910,427
[45] Date of Patent: Jun. 8, 1999

[54] ANTIGEN NON-SPECIFIC GLYCOSYLATION INHIBITING FACTOR DERIVATIVES

[75] Inventors: Toshifumi Mikayama, Gunma-machi; Takafumi Tomura; Hiroshi Watarai, both of Maebashi; Ryota Kuroki; Yoichi Kato, both of Yokohama; Kimishige Ishizaka, Yamagata; Tatsumi Nakano, Sapporo, all of Japan

[73] Assignee: La Jolla Institute for Allergy and Immunology, La Jolla, Calif.

[21] Appl. No.: 08/610,728

[22] Filed: Mar. 4, 1996

Related U.S. Application Data

[63] Continuation-in-part of application No. 08/503,646, Jul. 18, 1995, abandoned.

[30] Foreign Application Priority Data

Jun. 22, 1995 [JP] Japan ......................................... 155942

[51] Int. Cl.⁶ ........................... C12P 21/00; C07K 14/46; A61K 38/18
[52] U.S. Cl. .................... 435/69.1; 435/69.5; 435/252.3; 435/320.1; 530/350; 530/408; 530/402; 536/23.5; 424/85.1
[58] Field of Search ................................ 530/350, 350.1, 530/408, 402; 536/23.5; 424/85.1; 435/69.1, 69.5, 240.2, 252.3, 320.1

[56] References Cited

FOREIGN PATENT DOCUMENTS

WO 90/11301  10/1990  WIPO ............................. C07K 13/00
WO 94/26923  11/1994  WIPO ............................. C12P 21/02

OTHER PUBLICATIONS

Mikayama, et al., *Molecular cloning and functional expression of a cDNA encoding glycosylation–inhibiting factor*, Proc. Natl. Acad. Sci. USA, 90:10056, Nov. 1993.

Liu, et al., *Requirement of posttranslational modifications for the generation of biologic activity of glycosylation–inhibiting factor*, Proc. Natl. Acad. Sci. USA, 91:11227, Nov. 1994.

Suzuki, et al., *Crystallization and a Preliminary X–ray Diffraction Study of Macrophage Migration Inhibitory Factor from Human Lymphocytes*, J. Mol. Biol., 235:1141, 1994.

Alberts et al., Molecular Biology of the Cell, 1994, Garland Publishing, Inc., New York, NY, p. G16.

Sherman et al. Methionine or not methionine at the beginning of a protein. Bioessays, (Jul. 1985) 3 (1) 27–31.

*Primary Examiner*—Elizabeth Kemmerer
*Assistant Examiner*—David S. Romeo
*Attorney, Agent, or Firm*—Fish & Richardson P.C.

[57] ABSTRACT

Antigen non-specific human glycosylation inhibiting factor derivatives having the inmunosuppressive activity in which a mutation was introduced for replacement, deletion and/or insertion of a part of the amino acid sequence of SEQ ID NO:21, and/or which has received a chemical modification of one or more amino acid residue(s) in the amino acid sequence of SEQ ID NO:21, wherein the mutation and the chemical modification attenuate the strength of an intermolecular association in the region, which participates in trimerization, of an antigen non-specific human glycosylation inhibiting factor having the amino acid sequence of SEQ ID NO:21; DNAs containing a base sequence encoding the amino acid sequence of the antigen non-specific human glycosylation inhibiting factor derivative; recombinant vectors containing the DNAs; prokaryotic or eukaryotic cells transformed with the DNAs; methods of producing the antigen non-specific human glycosylation inhibiting factor derivatives; pharmaceutical compositions comprising the antigen non-specific human glycosylation inhibiting factor derivative and a pharmaceutically acceptable carrier; and methods of suppressing a human immune response to an antigen are provided.

28 Claims, 6 Drawing Sheets

ANTIGEN NON-SPECIFIC GLYCOSYLATION INHIBITING FACTOR DERIVATIVES

This application claims priority under §119 from Japan application 155942/1995, filed Jun. 22, 1995, and is a continuation-in-part of U.S. application Ser. No. 08/503,646, filed Jul. 18, 1995, abandoned.

FIELD OF THE INVENTION

The invention relates to antigen non-specific glycosylation inhibiting factor (hereinafter referred to as "GIF") derivative proteins which can be used to suppress the human immune response to antigens, DNAs encoding the GIF derivative proteins, recombinant expression vectors containing the DNAs, cells transformed with the DNAs, methods of producing the GIF derivative proteins, and pharmaceutical compositions comprising the GIF derivative proteins.

BACKGROUND OF THE INVENTION

It is well known that IgE antibodies against allergens (antigens) cause allergic diseases such as pollinosis. The role of IgE antibodies in the allergic diseases raised the possibility that the regulation and suppression of the IgE antibody formation against allergens would be one of the fundamental treatments of allergic diseases. In recent years, desensitization treatment in which allergic patients receive repeated injections of a minute dose of allergen is performed in actual clinical fields. Although the desensitization treatment can improve clinical symptoms in some patients, it involves the risk of causing anaphylactic shock. Hence, the desensitization treatment is performed only for limited patients under sufficient monitoring.

For the purpose of solving the aforementioned problem, an attempt was made to inject a modified antigen which does not bind to antibodies against native antigens. However, the IgE antibody titer of patients did not decline after the treatment. In the meantime, it was found that the injection of a modified antigen induced not only helper T cells but also antigen-specific suppressor T cells and that the transfer of the antigen-specific suppressor T cells suppressed ongoing IgE formation induced by immunization (Takatsu and Ishizaka, *J. Immunol.,* 117,:211, 1976). These findings suggest that it is possible to suppress ongoing IgE formation if antigen-specific suppressor T cells, not helper T cells, can selectively be induced without expanding the population of helper T cells.

In the 1980's, two types of T-cell factors that would bind to IgE for selectively regulating the IgE formation were found in the course of studies on the regulation of IgE formation. One of the IgE-binding factors enhances the IgE formation, while the other type of IgE-binding factor suppresses the IgE formation. The structures of the IgE-potentiating factors and IgE-suppressive factors are similar in protein moieties but different in carbohydrate moieties. The IgE-potentiating factor has a high-mannose N-linked carbohydrate and binds to lentil lectin. The IgE-suppressive factor does not have affinity for lentil lectin (Yodoi, et al, *J. Immunol.,* 128:289, 1982). It was shown that the IgE-potentiating factor and IgE-suppressive factor have different biological properties depending on the difference in the structure of the carbohydrate moieties. Under physiological conditions, the glycosylation process of the IgE-binding factors is controlled by two T-cell factors which either enhance or inhibit this process. A factor which enhances the glycosylation to produce the IgE-potentiating factor is denominated glycosylation enhancing factor (GEF) and a factor which inhibits the glycosylation to produce the IgE-suppressive factor is denominated glycosylation inhibiting factor (GIF). In experimental animals, GEF is always produced when the IgE formation is enhanced and GIF is always produced when the IgE formation is suppressed. Hence, it was believed that the balance of GEF and GIF would determine the properties of the IgE binding factors, thus controlling the IgE formation.

A subsequent study revealed that GIF-producing T cells were antigen-specific suppressor T cells (Jardieu et al., *J. Immunol.,* 133:3266, 1984). In a study using ovalbumin (OVA)-specific suppressor T cell hybridomas, it was found that the cells produced GIF constitutively and that the GIF did not exhibit specificity to antigens (antigen non-specific GIF). It was additionally found that the production of GIF having affinity for ovalbumin (antigen-specific GIF) was induced by stimulating the cells with ovalbumin and antigen-presenting cells. The antigen-specific GIF was composed of an antigen-binding polypeptide chain and a non-specific GIF (Jardieu and Ishizaka, Immune Regulation by Characterized Polypeptides, edited by Goldstein et al., Alan R. Liss, Inc., New York, page 595, 1987). It was revealed that the antigen-specific GIF shared common antigenic determinants with antigen-specific suppressor T-cell factors (Steele, J. K. et al., *J. Immunol.,* 142: 2213, 1989) and that the antigen-specific GIF suppressed the antibody response in an antigen (carrier)-specific manner (Jardieu, P. et al, *J. Immunol.,* 138:1494, 1987). It was also found that the production of ovalbumin-specific GIF was induced by injecting non-specific GIF into ovalbumin-primed mice and then stimulating their spleen cells with ovalbumin (Akasaki, M. et al, *J. Immunol.,* 136:3172, 1986).

Recently, the inventors have succeeded in isolating GIF from murine suppressor T cells and cloning a murine antigen non-specific GIF gene. Furthermore, they have obtained a human gene by using the GIF gene as a probe (Mikayama, T. et al., *Proc. Natl. Acad Sci. USA,* 90:10056, 1993). When the gene was expressed directly in *E. coli* or an animal cell as a host by a gene recombinant technique, the produced recombinant GIF exhibited extremely low biological activity compared to the GIF derived from suppressor T cells. Only when the gene was expressed in an animal host cell in the form of a fusion protein which is translocated into endo-plasmic reticulum, the produced recombinant GIF exhibited a biological activity comparable to the GIF derived from suppressor T cells. Thereafter, it was shown that some post-translational modification of GIF peptide was required for generation of a sufficiently high biological activity (Liu, Y-C. et al., *Proc. Natl. Acad Sci. USA,* 91:11227, 1994). As the structural studies of GIF are difficult to be accomplished with a limited amount of purified protein, structures essential for biologic activities are unknown at present.

It is expected that injections of antigen-specific GIF per se or non-specific GIF capable of inducing antigen-specific suppressor T cells is very effective in the treatments of allergy. Such treatment requires production of a large quantity of GIF having a sufficiently high biological activity by a recombinant DNA technique. However, since the molecular mechanisms for the generation of highly bioactive GIF is unknown, no one has ever succeeded in producing recombinant GIF derivative having a sufficiently high biological activity.

SUMMARY OF THE INVENTION

One objective of the invention is to provide GIF derivatives having a high biological activity.

Another objective of the invention is to provide methods by which a large amount of GIF derivatives having a high biological activity can be produced irrespective of procedures and hosts, as well as materials that are required for the methods.

A further object of the invention is to provide pharmaceutical compositions which can be used to suppress immune reactions against antigens for the treatments of diseases such as allergy.

The invention enables consistent, large scale production of GIF derivative proteins having a high immunosuppressive activity. The GIF derivative proteins can be used for the treatment and/or prevention of allergic diseases and the like.

DETAILED DESCRIPTION OF THE INVENTION

Figure 1:
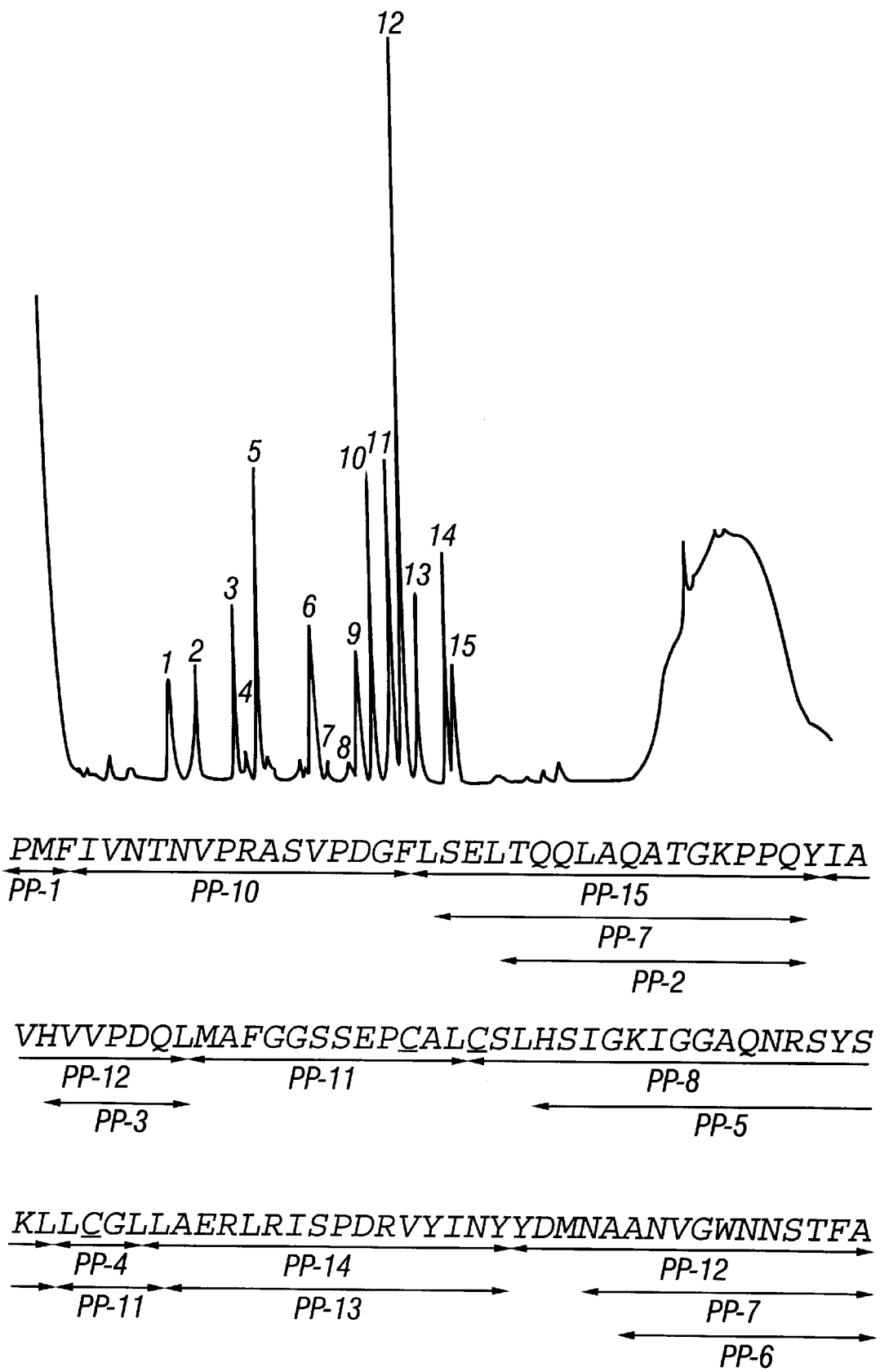
FIG. 1 shows a fractionation pattern of peptide fragments of pepsin-digested recombinant GIF in a Super ODS column and the amino acid sequences of the peptide fragments (Top sequence: residues 2–39 of SEQ ID NO:21; Middle sequence: residues 40–77 of SEQ ID NO:21; Bottom sequence: residues 78–115 of SEQ ID NO:21).

When GIF is produced by a recombinant DNA technique, the produced GIF has a lower biological activity compared to GIF produced by suppressor T cell hybridomas, except in the case where GIF is secreted and expressed in a mammalian host cell in the form of a fused protein with other proteins having a signal peptide for secretion. The inventors found that this does not result from undesired intramolecular disulfide bonds which often occur in recombinant proteins but that the GIF molecules form trimers by associating with themselves in a manner not mediated by disulfide bonds. In addition, they found that GIF derivatives having a high biological activity could be obtained by the introduction of a mutation and or chemical modification. The invention has been accomplished on the basis of these findings. The subject matters of the invention are as follows:

(1) An antigen non-specific human glycosylation inhibiting factor derivative having immunosuppressive activity in which a mutation was introduced for replacement, deletion and/or insertion of a part of the amino acid sequence of SEQ ID NO:21, and/or which has received a chemical modification of one or more amino acid residue(s) in the amino acid sequence of SEQ ID NO:21, wherein the mutation and or the chemical modification enhances the biological activity and immuno-suppressive effect of the wild-type non-specific human glycosylation inhibiting factor having the amino acid sequence of SEQ ID NO:21.

(2) A DNA containing a nucleotide sequence encoding the amino acid sequence of an antigen non-specific human glycosylation inhibiting factor derivative having immunosuppressive activity in which a mutation was introduced for replacement, deletion and/or insertion of a part of the amino acid sequence of SEQ ID NO:21, and/or which has received a chemical modification of one or more amino acid residue(s) in the amino acid sequence of SEQ ID NO:21, wherein the mutation and the chemical modification enhances biological activity and immunosuppressive effects of the wild-type antigen non-specific human glycosylation inhibiting factor containing the amino acid sequence of SEQ ID NO:21.

(3) A recombinant vector containing the DNA of (2).

(4) A prokaryotic or eukaryotic cell transformed with the DNA of (2).

(5) A method of producing an antigen non-specific human glycosylation inhibiting factor derivative, which comprises culturing the prokaryotic or eukaryotic cell of (4) and isolating and purifying the produced antigen non-specific human glycosylation inhibiting factor derivative.

(6) A method of producing an antigen non-specific human glycosylation inhibiting factor derivative, which comprises chemically modifying an antigen non-specific human glycosylation inhibiting factor or a derivative thereof in such a way as to attenuate the strength of an intermolecular association in the region of said inhibiting factor or derivative thereof which participates in trimerization.

(7) A pharmaceutical composition comprising the antigen non-specific human glycosylation inhibiting factor derivative of (1) and a pharmaceutically acceptable carrier.

(8) A method of suppressing a human immune response to an antigen which comprises administering to the human an immunosuppressively effective amount of the antigen non-specific human glycosylation inhibiting factor derivative of (1).

The invention will now be explained in detail.

The invention provides GIF derivative proteins having a high immunosuppressive activity (hereinafter referred to as "the protein(s) of the invention") irrespective of hosts and production processes.

The immunosuppressive activity of GIF (hereinafter referred to as "GIF activity") is defined as an activity to suppress the formation of specific antibody classified in antigen-induced immunoglobulins E and G in vivo. This activity can be determined as the ability by which murine T cell hybridoma 12H5 cells capable of producing glycosylated IgE-binding factor can be converted to those capable of producing non-glycosylated IgE-binding factor in vitro (Iwata and Ishizaka, *J. Immunol.*, 141:3270, 1988).

The proteins of the invention are antigen non-specific human glycosylation inhibiting factor derivatives having the immunosuppressive activity in which a mutation was introduced for replacement, deletion and/or insertion of a part of the amino acid sequence of SEQ ID NO: 1, and/or which has received a chemical modification of one or more amino acid residue(s) in the amino acid sequence of SEQ ID NO:21. The mutation and or the chemical modification results in enhanced biological activity of GIF molecules and may attenuate the strength of an intermolecular association in the region which participates in trimerization of an antigen non-specific human glycosylation inhibiting factor containing the amino acid sequence of SEQ ID NO:21. The strength of the intermolecular association can be measured by light scattering, analytical ultracentrifuge, crystallographic analysis and the like and is preferably less than 614 Abs$^{-2}$ to exhibit high GIF activity.

The mutation which attenuates the strength of the intermolecular association includes the replacement, deletion and insertion of at least one amino acid residue which will change an intermolecular interaction (particularly due to hydrogen-bond formation and hydrophobic interaction) at a site to be subjected to a mutagenesis. Examples of the mutation include replacement, deletion, insertion and addition which change the polarity of a region participating in association (e.g., replacement of a neutral amino acid residue with a charged amino acid residue and vice versa, insertion or deletion of a charged amino acid residue, etc.), replacement of an amino acid residue in a region participating in association with one having a side chain of a different length and the like. Another examples is the mutations of an amino acid residue which is outside the region of interest but which is within a region that affects the structure of that region such as to attenuate the strength of the association.

Preferred mutation sites include amino acid residues in a region which is believed to participate in an intermolecular association for trimerization, regions adjacent thereto and regions affecting the structure of that region. Examples of the region which is believed to participate in intermolecular association include the 37–45, 47–50, 94–98 and 106–110 positions which participate in intermolecular hydrogen-bond network formation, as well as the 39, 48, 50, 57 and 59 positions which participate in cluster formation mainly due to a hydrophobic interaction of the molecule with the amino acid sequence of SEQ ID NO:21. Specific examples of the mutation include a replacement of cysteine residue with alanine or serine residue at the 57 position, a replacement of cysteine and asparagine residues with alanine and serine residues at the 57 and 106 positions, respectively, and the like.

The modification which attenuates the intermolecular association includes the selective chemical modifications of amino acid residues of proteins that are known hitherto and which increase or decrease the charge on or hydrophobic property of an amino acid residue to be modified, as exemplified by phosphorylation, alkylation, acylation, modifications of sulfhydryl group(s) of cysteine residues. Specific examples of the modification include carboxymethylation, pyridylethylation and ethylmercurithiosalicylate (EMTS) or 5,5'-dithiobis(2-nitrobenzoic acid)) (DTNB) for selective chemical modification of cysteine residues, acetylation for modification of the N-terminus and formylation and the like.

The selective chemical modifications can apply to not only the GIF protein containing the amino acid sequence of wild type but also the GIF proteins which have a mutation introduced for replacement, deletion and/or insertion of amino acid sequence of wild type GIF (SEQ ID NO:21). The examples of chemical modifications of the mutant GIF protein include, but are not limited to, carboxymethylation of the mutant GIF whose cysteine residue at 57 position is replaced with alanine residue and whose cysteine and asparagine residues at the 57 and 106 positions are replaced with alanine and serine residues respectively.

The invention also provides DNAs encoding GIF derivative proteins having a high immunosuppressive activity (hereinafter referred to as "the DNA(s) of the invention"). The DNAs of the invention are DNAs containing a nucleotide sequence encoding the amino acid sequence of an antigen non-specific human glycosylation inhibiting factor derivative having the immunosuppressive activity of a glycosylation inhibiting factor, which has a mutation introduced for replacement, deletion and/or insertion of part of the amino acid sequence of SEQ ID NO:21, wherein the mutation attenuates the strength of an intermolecular association, particularly in the region, which participates in trimerization, of an antigen non-specific human glycosylation inhibiting factor containing the amino acid sequence of SEQ ID NO:21. These DNAs can be prepared by site-directed mutagenesis using a known GIF cDNA (Mikayama, T. et al., supra), by chemical synthesis of a partial DNA containing the mutation site of interest and replacement of the corresponding site of GIF cDNA with the synthesized DNA, or by complete chemical synthesis.

The DNAs of the invention include DNAs containing any nucleotide sequences that are degenerate as a result of the genetic code. If preferred codons which are suitable for a host in which the GIF derivative protein is to be expressed are selected for a partial or entire GIF-encoding region, the expression level of the protein can be raised. Particularly, in the case where preferred codons are selected for a partial GIF-encoding region, it is effective to select them for the N-terminus encoding region.

Examples of the DNAs of the invention include DNAs containing the nucleotide sequence of SEQ ID NO:2, 3 or 20, and the like.

The DNAs of the invention may receive insertion of restriction sites and/or DNA addition to the initiation and termination sites for the construction of expression vectors to facilitate the expression.

The invention provides vectors incorporating the DNA of the invention, host cells transformed with the vectors, and methods of producing the protein of the invention which comprise culturing the host cells and isolating and purifying the produced protein of the invention.

As host cells, prokaryotic organisms (e.g., bacteria, preferably *E. coli*), cells of eukaryotic organisms (e.g., yeast, insects and mammals) can be used. Examples of the mammalian cells include COS cells, Chinese Hamster Ovary cells, X63.6.5.3. cells, C-127 cells, BHK (Baby Hamster Kidney) cells, human-derived cells (e.g., HeLa cells) and the like. Examples of yeast include *Saccharomyces cerevisiae, Pichia pastoris* and the like. Examples of insect cells include *Bombyx mori* cultured cells (e.g., Sf21 cells) and the like.

The vectors to be used to transform these host cells include pKC30 (Shimatake H. and M. Rosenberg, *Nature,* 292:128, 1981) and pTrc99A (Amann E. et al., *Gene,* 6:69, 301, 1988) and the like for expression in *E. coli*; pSV2-neo (Southern and Berg, *J Mol. Appl Genet.,* 1:327, 1982), pCAGGS (Niwa, et al., *Gene,* 108:193, 1991) and pcDL-SRα296 (Takebe, et al., *Mol. Cell. Biol.,* 8:466, 1988) and the like for expression in mammalian cells; pG-1 (Schena M. and Yamamoto K. R., *Science,* 241:965, 1988) and the like for expression in yeast; and transfer vector pAc373 for recombinant virus preparation (Luckow, et al., *Bio/Technology,* 6:47, 1988) and the like for expression in *Bombyx mori* cultured cells.

These vectors may contain an origin of replication, selective markers, a promoter, if necessary. The vectors for expression in eucaryotic cells may contain RNA splice sites, a polyadenylation signal and the like, if necessary.

As origins of replication, those derived from SV40, adenovirus and bovine papilloma virus and the like can be used for the vectors for expression in mammalian cells. Origins of replication derived from Col E1, R factor and F factor can be used for the vectors for expression in *E. coli*. Origins of replication derived from 2mDNA and ARS1 can be used for the vectors for expression in yeast.

As promoters for gene expression, those derived from virus such as retrovirus, polyoma virus, adenovirus, SV40 and the like, and those derived from chromosomes (e.g., EF1α) can be used for the vectors for expression in mammalian cells. Promoters derived from bacteriophage λtrp, lpp, lac and tac promoters can be used for the vectors for expression in *E. coli*. ADH, PHO5, GPD, PGK, MAF α promoters can be used for the vectors for expression in *Saccharomyces cerevisiae* and AOX1 promoter and the like can be used for the vectors for expression in *Pichia pastoris*. Promoters derived from nuclear polyhidrosis virus and the like can be used for the vectors for expression in *Bombyx mori* cultured cells.

As selective markers, neomycin (neo)-resistance gene, thymidine kinase (TK) gene, dihydrofolate reductase (DHFR) gene, *E. coli* xanthine guanine phosphoribosyl transferase (Ecogpt) gene and the like can be used for the vectors for expression in mammalian cells. Kanamycin-resistance gene, ampicillin-resistance gene, tetracycline-resistance gene and the like can be used for the vectors for expression in *E. coli*. Leu2, Trp1, Ura3 genes and the like can be used for the vectors for expression in yeasts.

The proteins of the invention produced in the aforementioned host-vector systems can be obtained as follows:

A host cell is transformed with a recombinant DNA incorporating the DNA of the invention at an appropriate site and subsequently cultured, followed by the isolation and purification of the protein of the invention from the cultured cells or medium. Known procedures and techniques may be used in combination to produce the proteins.

Techniques for the purification include processes generally used for protein purification (ion-exchange chromatography, hydrophobic interaction chromatography, gel permeation chromatography, reversed-phase chromatography, is electric chromatography, preparative chromatography, is electric electrophoresis and the like) and combinations thereof. Methods of purification include affinity-purification using GIF-recognizing antibodies (WO94/26923).

The invention also provides methods of producing the chemically modified protein of the invention which comprise chemically modifying GIF containing the amino acid sequence of wild-type or a derivative thereof in such a way as to attenuate the strength of an intermolecular association, particularly in the region, which participates in trimerization, of the antigen non-specific human glycosylation inhibiting factor or derivative thereof. More specifically, the proteins of the invention can be prepared by combining to the GIF containing the amino acid sequence of wild types or a derivative thereof a modification group which increases or decreases the charge on or hydrophobic property of the amino acid residue to be modified, and subsequently separating and purifying the product.

Specific examples of the chemical modification include phosphorylation, alkylation, acylation, EMTS- or DTNB-modification and the like; more specific examples include carboxymethylation and pyridylethylation for selective chemical modification of cysteine residues, acetylation for modification of the N-terminus, formylation and the like.

Phosphorylation can be performed by an enzymatic reaction in which the γ-phosphoryl group of ATP is transferred to the hydroxy group of serine, threonine or tyrosine with protein kinase.

Alkylation of SH group can be performed with a compound containing a halogenated alkyl group (monoiodoacetic acid and amides thereof, monobromoacetic acid and amides thereof, α-iodopropionic acid, β-bromoethylamine, monochloroacetic acid, chloroacetophenone and the like). For example, a lipid such as farnesyl group can be introduced with farnesyl bromide. The modification of amino groups can be performed with an aliphatic aldehyde, a ketone containing a carbonyl group and the like.

Acylation can be performed with a carboxylic anhydride, carboxylic chloride or a dehydration condensing agent such as the combination of carboxylic acid with carbodimide by a reaction in which the hydrogen atom of hydroxy, sulfhydryl or amino group is substituted with an acyl group. For example, N-acetyl imidazole, N-acetyl succinimide and the like can be used to acetylate amino groups. The condensation of polyethylene glycol having a carboxy group at the end with N-hydroxysuccinimide using carbodimide through dehydration produces an activated PEG capable of reacting with amino groups and the activated PEG can be added to the N-terminus of the protein. After glycine is added to the N-terminus of the proteins, myristoylation can be performed; alternatively palmitoylation, retinoylation and lipoylation can be performed in the case of tyrosine, threonine, cysteine and the like.

Thiol reagent such as EMTS or DTNB or methyl methane thiosulfate can be used to modify cysteine residues of the protein.

Specific examples of the modification with a macromolecular compound include a method of combining a soluble dextrin (Wileman, T. E. et al., *J. Pharm. Pharmacol.,* 33: 85, 1982), a method using poly-DL alanine (Uren, J. R. et al., *Cancer Res.,* 42:4068, 1982) and the like.

The level of the modification can be estimated by determining the amount of unreacted reactive groups of the protein. For example, unreacted SH groups can be determined by Ellman's method (Glazer, A. N., The Proteins, 3rd., II, Academic Press, New York, 1976) in the case where free SH groups of cysteine residues are modified with monoiodoacetic acid or 4-vinylpyridine and then S-carboxymethylated or S-pyridylethylated.

When tyrosine residues are modified with an iodinating agent (e.g., triodide ion ($I^{-3}$), iodine chloride, etc.), histidine residues with diethylpyrocarbonate, and arginine residues with phenyl glyoxal, the amount of unreacted amino acid residues can be estimated by an amino acid composition analysis or by the change in ultraviolet absorption spectrum. In the case where a modification causes a great change in the molecular weight of the protein, the level of the modification can be estimated by tracing the change in the mobility of the modified protein by sodium dodecyl sulfate polyacrylamide gel electrophoresis (SDS-PAGE). Peptide mapping can be used to determine which amino acid residues have been modified.

The modified proteins can be isolated and purified by known procedures and techniques, and combinations thereof as described in connection with the methods of producing the mutant proteins of the invention by gene recombination.

The invention also provides pharmaceutical compositions comprising the protein of the invention as an active ingredient (hereinafter referred to as "the pharmaceutical compositions of the invention"). The pharmaceutical compositions of the invention can be used for immunosuppression, more specifically, for alleviation and/or prevention of undesired immune responses in a human to be treated. The undesired immune responses, that is, adverse immune responses against antigens, include rheumatoid arthritis, autoimmune diseases such as multiple sclerosis, diabetes and the like, allergic diseases against a variety of antigens, host versus graft (HVG) and graft versus host rejections and the like. In an embodiment of the present invention, the pharmaceutical compositions of the invention can be used for the treatment and/or prevention of diabetes. The invention encompasses pharmaceutical compositions comprising a therapeutically effective amount of the protein of the invention and a pharmaceutically acceptable carrier. The pharmaceutical compositions may contain a diluent, antiseptic, solubilize, emulsifying agent and other adjuvants. The term therapeutically effective amount" means an amount which provides a therapeutic effect under given conditions by a given method of administration. The pharmaceutical compositions may be preparations in liquid, lyophilized or dried forms which are formulated with the following: diluents selected from buffering agents having various pH values and ionic strengths such as Tris-HCl, acetates and phosphates; additives which prevent surface adsorption such as albumin and gelatin; surfactant such as Tween 20, Tween 80, Pluronic F68 and bile acid salts; solubilizers such as glycerol and polyethylene glycol; antioxidants such as ascorbic acid and sodium metabisulfite; antiseptics such as thimerosal, benzyl alcohol and parabens; vehicles and tonicity agents such as lactose and mannitol. The proteins of the invention as active ingredients may form complexes with metal ions, may be incorporated in particulate preparations containing a polymerized compound such as polylactic acid, polyglycolic acid or hydrogel or adsorbed on the surface thereof, or may be incorporated in liposomes, micro emulsions, micelles, monolayer or multi layer vesicles, erythrocyte membrane ghosts and spheroplast. Since the pharmaceutical compositions will influence the physical states, solubility, stability, in vivo release rate and in vivo clearance of the proteins of the invention, the selection of the pharmaceutical compositions depends on the physical and chemical properties of the proteins of the invention as active ingredients. The pharmaceutical compositions of the invention can be administered transplumonarily, transnasally, orally, intravenously, intraperitoneally, intramuscularly, subcutaneously, within cavities, or transdermally. They may be in a particulate form and provided with protective coatings, protease inhibitors or absorption enhances, depending on the administration routes, if desired.

The proteins of the invention can be administered generally at a dose varying from 0.001 mg/kg to 2 mg/kg, in one or more dose administrations daily, for one or several days, depending on the age, condition, sex and extent of the disease in the patient and the administration route.

The invention will now be explained in greater detail with reference to the following examples which are provided herein for the purpose of illustration only, and are not intended to limit the scope of the invention.

EXAMPLE 1

Expression in *E. Coli* of GIF Derivatives Having Replacement of Cysteine Residue

A. CONSTRUCTION OF EXPRESSION SYSTEM

This example relates to the expression of GIF derivatives having replacement of cysteine residue. Three cysteine residues in a GIF polypeptide at the 57, 60 and 81 positions were each replaced with alanine residue by introducing a mutation into a nucleotide at the corresponding site of the GIF gene of SEQ ID NO:1.

Polymerase chain reaction (PCR, Mullis, et al., *Method in Enzymol.*, 155:335, 1987) was performed using as template DNA the expression plasmid pTMK-hGIF (WO94/26923, supra) which comprises human GIF cDNA inserted into expression vector pST811 for expression in *E. coli* (Japanese Unexamined Patent Publication No. Sho 63-269983) with the following oligonucleotide primers being also used.

5'-AACCTTAAGAAAAACCAAGGAGGTAATAAATA ATGCCGATGTTCATCGTAAACACCAACG-3' (primer #1: SEQ ID NO: 4)

3'-CTCGGCCGGCGCGAGACGTCGGAC-5' (SEQ ID NO: 5)

Each PCR cycle consisted of denaturation at 95 ° C. for 1 minute, annealing at 56° C. for 2 minutes and elongation at 72° C. for 2 minutes. All PCR stages were performed under the same conditions as described above. Amplified DNA fragments were recovered from an agalose gel and digested with AflII and PstI.

In a separate step, pTMK-hGIF was cleaved with PstI and BamHI and 3'-end DNA fragment of GIF cDNA was recovered. These fragments were inserted using DNA ligase into vector pST811 cleaved with AflII and BamHI. The obtained expression plasmid contained human GIF cDNA in which the cysteine residue was replaced with an alanine residue at the 57 position as shown in SEQ ID NO: 2 and it was denominated pC57A-hGIF.

In a similar manner, expression plasmid pC60A-hGIF containing human GIF cDNA in which the cysteine residue was replaced with an alanine residue at the 60 position was constructed as follows:

PCR was performed using pTMK-hGIF as a template, with primer #1 and the following oligonucleotide primer being also used.

3'-CGCGAGCGATCGGACGTGTCGTAG-5' (SEQ ID NO: 6) Amplified DNA fragments were recovered and digested with AflII and NheI.

A 3'-end DNA fragment was prepared using the following primers:

5'-GCGCTCGCTAGCCTGCACAGCATC-3' (SEQ ID NO: 7)

3'-CACCCGACCTTGTTGAGGTGGAAGCGGATTATC CCTAGGCAA-5' (primer #2: SEQ ID NO: 8)

Amplified DNA fragments were recovered and digested with NheI and BamHI. These fragments were inserted into vector pST811 that had been cleaved with AflII and BamHI. Expression plasmid pC81A-hGIF containing human GIF cDNA in which the cysteine residue was replaced with an alanine residue at the 81 position was constructed as follows: PCR was performed using pTMK-hGIF as a template, with primer #1 and the following primer being also used.

3'-GGCCAGCAGGCCGGCTAGCAGCTT-5' (SEQ ID NO: 9) Amplified DNA fragments were recovered and digested with AflII and NheI.

A 3'-end DNA fragment was prepared using primer #2 and the following primer:

5'-AAGCTGCTAGCCGGCCTGCTGGCC-3' (SEQ ID NO: 10)

Amplified DNA fragments were recovered and digested with NheI and BamHI. These fragments were inserted into vector pST811 that had been cleaved with AflII and BamHI. Each expression plasmid was transformed into a competent RR1 *E. coli* host cell.

The DNA sequences of the primers used for the construction of the expression systems and those of the DNA fragments amplified by PCR were confirmed by conventional DNA sequencing.

B. CULTURE OF *E. coli* PRODUCING A GIF DERIVATIVE

RR1 *E. coli* carrying expression plasmid pC57A-hGIF, pC60A-hGIF or pC81A-hGIF were cultured in 20 ml of Luria broth containing 50 mg/liter of ampicillin overnight at 37° C. The inoculum culture was transferred to 1 liter of M9 broth which was composed of 0.8% glucose, 0.4% casamino acid, 10 mg/liter of thiamin and 50 mg/liter of ampicillin and cultured for 3 hours at 37° C. At the end of this initial incubation, 40 mg of indole acrylic acid was added and the culture was incubated for an additional 5 hours at 37° C.

EXAMPLE 2

Purification of Recombinant GIF Derivative Products

This example relates to a method of purifying recombinant GIF derivative proteins expressed in *E. coli* to such an extent that it can be administered in vivo.

About 5 g wet weight of the *E. coli* cells which were cultured in Example 1 were harvested and suspended in 30 ml of water, followed by breaking them by French-Press (8000 psi repeated 4 times). Supernatant and broken cell pellets were separated by centrifugation at 15000×g for 10 minutes. The supernatant were recovered. The expression of GIF derivative proteins was confirmed by SDS-PAGE.

The GIF derivative protein encoded in expression plasmid pC57A-hGIF was denominated C57A-GIF. Similarly, the GIF derivative proteins encoded in expression plasmids pC60A-hGIF and pC81A-hGIF were denominated C60A-GIF and C81A-GIF, respectively.

Sodium acetate buffer (pH 5.5) was added to the GIF derivative protein at a final concentration of 20 mM and the resulting solution was applied to a CM-Sepharose Fast Flow (Pharmacia) column (5×18 cm) equilibrated with the same buffer at 4° C. The column was washed with 20 mM sodium acetate buffer (pH 5.5) and 0.3M NaCl in 20 mM sodium acetate buffer (pH 5.5) at a flow rate of 2 ml/min. The GIF derivative protein was eluted with 0.5M NaCl in 20 mM sodium acetate buffer (pH 5.5).

The eluted fractions were dialyzed against 100 volumes of 20 mM sodium acetate buffer (pH 5.5) and applied to TOSOH CM-5PW (TOSOH) column (0.75×7.5 cm) equilibrated with the same buffer. The column was washed with 20 mM sodium acetate buffer (pH 5.5) at a flow rate of 1 ml/min and the GIF derivative protein was eluted with a gradient of 0 to 0.5M NaCl at room temperature.

GIF derivative protein-containing fractions were determined by SDS-PAGE and the western blot technique using anti-GIF antibodies (WO94/26923, supra).The purities of C57A-GIF, C60A-GIF and C81A-GIF obtained by the above procedures were determined to be more than 99%. After the buffer was replaced with PBS solution by dialysis, these samples were stored.

For the purpose of completely removing endotoxin derived from *E. coli*, a 1/10 volume of PyroSep C (DAICEL CHEMICAL INDUSTRIES, LTD.) was added to the purified sample and the mixture was stirred for 1–12 hours, if necessary. The supernatant was recovered. The amount of endotoxin was determined with a Limulus ES-II Single Test (WAKO PURE CHEMICAL INDUSTRIES, LTD.).The concentration of the GIF derivative proteins was determined by measurement of absorbance at a wavelength of 280 nm and calculation using molar extinction coefficient of each derivative obtained by amino acid composition analysis.

EXAMPLE 3

Biological Activity of Recombinant GIF Derivatives

This example relates to the in vivo activity of the recombinant GIF derivatives prepared in Example 2. The in vivo IgE antibody formation-inhibiting activity of the recombinant GIF derivatives was estimated. For use as a control in activity comparison, an *E. coli* derived recombinant human GIF protein containing an amino acid sequence of a wild type, which was already found to have in vivo IgE and IgG1 antibody formation-inhibiting activities, was produced by the same procedure as in Examples 1B and 2 except that the expression plasmid was pTMK-hGIF (WO94/26923, supra).

BDF1 mice were immunized by an intraperitoneal injection of 0.1 µg DNP-ovalbumin absorbed to 1 mg of alum. The recombinant GIF and derivatives thereof were each injected i.p. the day before immunization and on days 0, 1, 2, 3, 4, 6, 8 and 10. The control mice received PBS alone.

Two and three weeks after immunization, blood was collected from each mouse and anti-DNP-IgE and anti-DNP-IgG1 levels in sera were measured by ELISA. The results showed that C57A-GIF had a higher activity than the control recombinant GIF (Table 1).

The GIF bioactivity of the same preparations was assessed by the ability of this cytokine to switch the murine T cell hydridoma 12H5 cells from the formation of glycosylated IgE-binding factor to the formation of unglycosylated IgE-binding factor (Iwata et al, *J. Immunol.* 140:2534, 1988). Aliquots of a suspension of the hybridoma cells was cultured for 24 hr with 10 µg/ml mouse IgE in the presence of a sample to be tested. Culture supernatant were filtered through CF50A membrane, and IgE-binding factors in the filtrates were fractionated on lentil lectiv Sepharose (Yodoi et al., *J Immunol.*, 125:1436, 1980). The factors in the flow through fraction and those retained in the column were assessed by rosette inhibition techniques. If a sufficient amount of GIF were present in a test sample, the majority of IgE-binding factors formed by the 12H5 cells lacked affinity for lentil lectin, and were recovered in the flow through fraction (Iwata & Ishizaka, *J. Immunol.*, 141:3270, 1988). The minimum concentration of wild type GIF or its derivative for the detection of the GIF bioactivity is included in Table 1.

TABLE 1

ACTIVITY OF RECOMBINANT GIF AND DERIVATIVES THEREOF

| Sample | N | Anti DNP-IgE (ng/ml) | Minimal concentration in vitro GIF bioactivity (ng/ml) |
|---|---|---|---|
| PBS (Control) | 6 | 409 ± 75 | — |
| GIF | 4 | 345 ± 125 | >1000 |
| C57A-GIF | 4 | 197 ± 74 | 125 |
| C60A-GIF | 4 | 304 ± 110 | 250 |
| C81A-GIF | 4 | 375 ± 155 | >1000 |

EXAMPLE 4

Absence of Intramolecular S—S Bonds in Recombinant GIF and Derivatives Thereof

This example verifies that the recombinant GIF and derivatives thereof do not have any intramolecular S—S bonds.

1) The recombinant GIF or derivatives thereof (2.4 µg) whose biological activities were determined in Example 3 were dissolved in 0.2M sodium acetate buffer (pH 4.0). To the solution was added a 1/25 amount of pepsin (Sigma) and the mixture was left to stand for 7 hours at room temperature to digest the protein. The sample solution was applied to Super ODS (TOSOH) column (0.2×5 cm) equilibrated with 95% solution A (0.05% trifluoroacetic acid) and 5% solution B (0.02% trifluoroacetic acid, 70% isopropanol and 30% acetonitrile). The column was washed at a flow rate of 0.2 ml/min for 5 minutes. The ratio of solution B was increased linearly to 25% over 40 minutes and to 100% over an additional 5 minutes to recover the fractions of fragmented peptides. The amino acid sequences of all the recovered peptides were determined by using a gas-phase amino acid sequencer PPSQ 10 (Shimadzu). As a result, it was revealed that three kinds of peptides containing one cysteine residue were fractionated separately, indicating that no cysteine residues cross linked each other through S—S bonds. A fractionation pattern of the peptides obtained by the treatment of the recombinant GIF or derivatives thereof with pepsin and the amino acid sequences of the peptides are shown in FIG. 1.

For confirmation, the following experiment was conducted. Dithiothreitol (DTT) was added to the sample digested with pepsin at a final concentration of 10 mM and the mixture was left to stand for 30 minutes at room temperature. The sample solution was applied to Super ODS column and the above procedure was repeated. The elution patterns of the peptides were the same for all the recombinant GIF and derivatives thereof.

2) It is generally known that a disulfide bond plays an important role in retaining the stability of proteins. If a disulfide bond exists in the molecule, the replacement of cysteine with alanine should make the protein molecule significantly unstable. The transition temperatures of mutant proteins C57A-GIF and C81A-GIF in which one of three cysteine residues in the recombinant GIF was replaced with alanine were determined in 50 mM acetate buffer (pH 5.5) to be 68.7 and 71.6, respectively. These temperatures were almost consistent with that of a wild type (70.9 ). This indicates that the three cysteine residues did not form any disulfide bonds.

3) The distances between ionized atoms in the three cysteine residues, that is, those of S-(Cys57)-S(Cys60), S(Cys57)-S(Cys81) and S(Cys60)-S(Cys81), in *E. coli* produced recombinant human GIF protein containing an amino acid sequence of a wild type, were determined by X-ray crystallography to be about 10 Å, 13 Å and 8 Å, respectively. The formation of disulfide bond requires these interatomic distances to be about 2.0 Å or less. The results of X-ray crystallography revealed that the three cysteine residues are positioned at longer distances than about 2.0 Å in the tertiary structure, indicating that the GIF cannot form any disulfide bonds in the molecule.

EXAMPLE 5

Presence of Recombinant GIF as a Trimer

A. ESTIMATION OF THE MOLECULAR WEIGHT OF RECOMBINANT GIF

Figure 2:
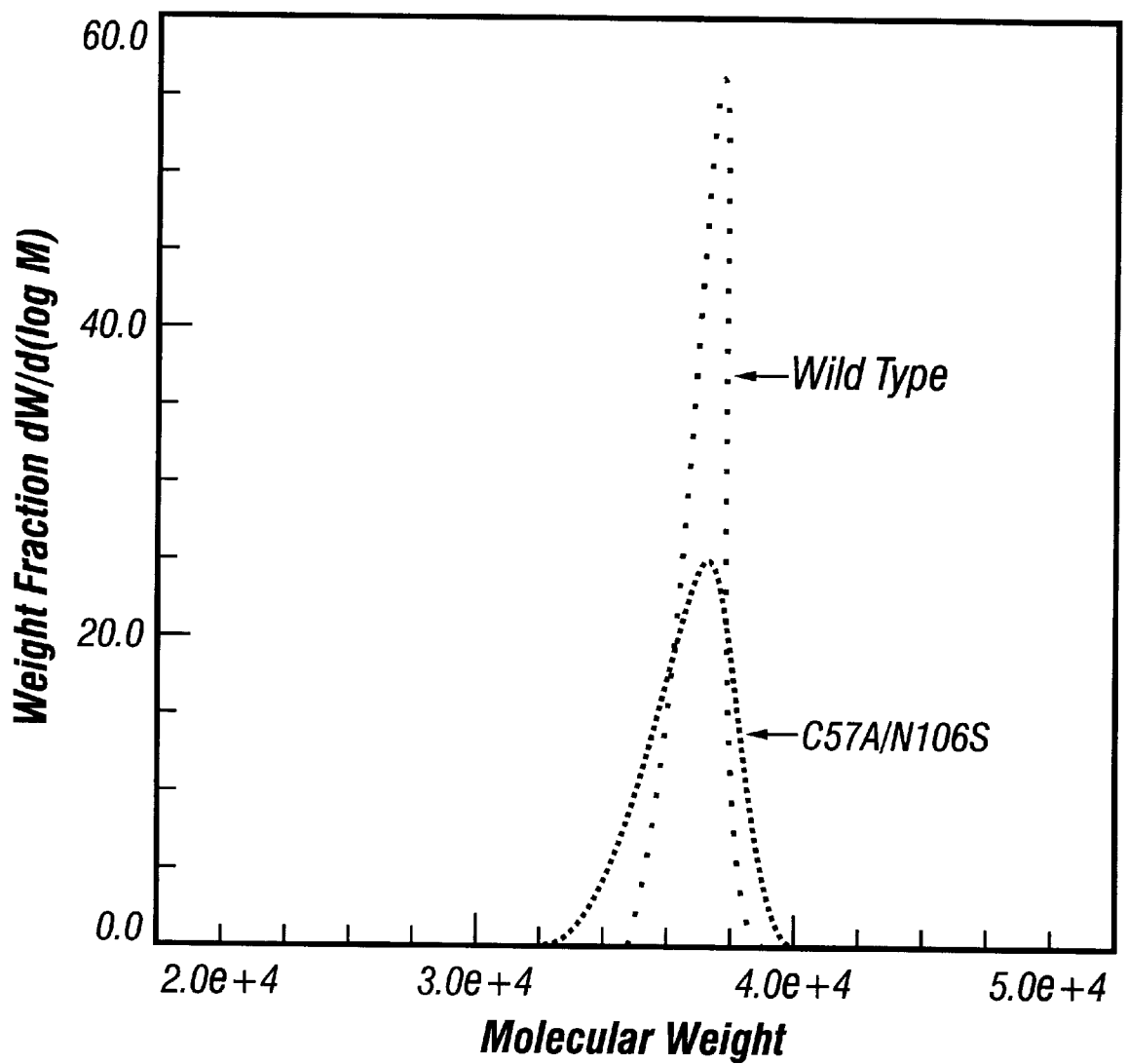
FIG. 2 shows the molecular weight distribution of recombinant GIF (wild type) and C57A/N106S-GIF as measured by light scattering.

The recombinant GIF containing the amino acid sequence of a wild type which was used as a comparative control in Example 3 was dissolved in PBS at a concentration of 1.2 mg/ml and the sample solution was applied to Shodex KW803 (Showa Denko K.K.) equilibrated with 0.1M NaCl in 50 mM phosphate buffer (pH 6.8). The absolute molecular weight of the protein eluted at a flow rate of 1.0 ml/min was measured by using WYATT DAWNDSP-F light-scattering photometer (Wyatt). FIG. 2 shows the measured molecular weight distributions a result of the calculation in which dn/dc=0.180 cm$^3$/g and A2=0, the molecular weight was estimated to be 36,490.

Subsequently, the recombinant GIF was dissolved in PBS at a concentration of 0.68 mg/ml. The sample solution was centrifuged at 17000 rpm for 15 hours at 20° C. by using analytical ultracentrifuge Optima XL (Beckman) to determine the average molecular weight. As a result, the GIF protein was found to have an average molecular weight of 32013. The association constant was calculated to be 614.18.

These results show that the recombinant GIF protein exists as a trimer.

B. CRYSTALLOGRAPHY OF RECOMBINANT GIF

The recombinant GIF was crystallized by a vapor diffusion method. More specifically, the GIF protein (20 mg/ml) was dissolved in 100 mM HEPES buffer (pH 7.5) containing 2.0M ammonium sulfate and 2% (w/v) PEG 400 and the resulting solution was left to stand at 4° C. A crystal having a length of about 0.5 mm was obtained in about 1–2 weeks.

The crystals of heavy atom derivatives were prepared from the above crystal of the recombinant GIF by a soaking method. One of the crystals was prepared by immersing the crystal of the recombinant GIF in 100 mM HEPES buffer (pH 7.5) containing 0.2 mM HgCl$_2$, 2.6M ammonium sulfate and 2% (w/v) PEG 400 for 5 days. The other crystal was prepared in the same manner except that the HEPES buffer containing 1.0 mM ethylmercurithis salicylate (hereinafter referred to as "EMTS") instead of 0.2 mM HgCl$_2$ was used. All reactions were conducted at 4 ° C.

Data were obtained by using an IP difractometer. A portable X-ray generator (4 kW) was used. The measurements were carried out at a resolution of 2.3 Å for 30 hours for the crystal of the recombinant GIF, 2.5 Å×25 hours for the crystal of the HgCl$_2$-treated heavy atom derivative, and 2.7 Å×40 hours for the crystal of the EMTS-treated heavy atom derivative.

For structural analysis, multiple isomorphous replacement method was used for phase calculation, and a solvent flattening method and a molecular averaging method were used for phase modification. The analysis of molecular structure (the trace of main chain and the assignment of side chains) and the construction of a molecular model were carried out on the basis of the obtained data, revealing that the recombinant GIF was trimerized through the association which took place as a result of the intermolecular hydrogen-bond network formation between the region of the 37–45 positions and that of 47–50 positions and between the region of 94–98 positions and that of 106–110 positions, as well as due to the cluster formation mainly by the hydrophobic interaction between the 39, 48, 50 and 57 positions.

EXAMPLE 6

The Production in *E. coli* of GIF Derivatives Having Replacement of an Additional Amino Acid Residue Other Than Cysteine, the Biological Activity and the Structure Thereof A . PRODUCTION IN *E. coli* OF GIF DERIVATIVES IN WHICH THE AMINO ACID RESIDUE WAS REPLACED AT THE 106 POSITION Completely synthesized DNA (Code#BBG54) commercially available from BBL Co. was purchased. This DNA encodes an amino acid sequence which is different from the amino acid sequence of SEQ ID NO:1 only in the point that the asparagine residue is replaced with a serine residue at the 106 position (SEQ ID NO: 11). The mutation in which cysteine residues were replaced with alanine at the 57 or 81 position was introduced in the DNA by the same method as in Example 1 and the DNA having this mutation was expressed in *E. coli* by using expression vector pST811. The expressed recombinant GIF proteins were purified by the same method as in Example 2 except that the GIF proteins were eluted with 0.3M NaCl. The obtained GIF derivatives having a mutation in two amino acids were denominated C57A/N106S-GIF and C81A/N106S-GIF.

B. BIOLOGICAL ACTIVITY OF C57A/N106S-GIF AND C81A/N106S-GIF

The above recombinant GIF derivatives were evaluated for antibody formation-inhibiting activity by the same in vivo assay as in Example 3 except that 20 μg of the recombinant GIF derivatives were injected. As a result, C57A/N106S-GIF exhibited a higher activity than C81A/N106S-GIF (Table 2).

TABLE 2

ACTIVITY OF RECOMBINANT GIF DERIVATIVES

| Sample | N | Anti DNP-IgE (ng/ml) |
|---|---|---|
| PBS (Control) | 10 | 84.3 ± 21.0 |
| C57A/N106S-GIF | 4 | 27.2 ± 8.2 |
| C81A/N106S-GIF | 4 | 86.3 ± 17.5 |

In another experiment where the frequency of the injection of the GIF derivatives was reduced to 6 times (the day before immunization, on days 1, 3, 6, 8 and 10), C57A/N106S-GIF exhibited a higher activity than C57A-GIF (Table 3).

TABLE 3

ACTIVITY OF RECOMBINANT GIF DERIVATIVES

| Sample | N | Anti DNP-IgE (ng/ml) |
|---|---|---|
| PBS (Control) | 6 | 345.1 ± 128.6 |
| C57A-GIF | 4 | 127.1 ± 42.5 |
| C57A/N106S-GIF | 4 | 61.3 ± 20.4 |

C. STERIC STRUCTURE OF C57A/N106-GIF

The molecular weight distribution of C57A /N106S-GIF was measured by the same method as in Example 5 using a light-scattering photometer. The results show that C57A/N106S-GIF was trimerized as in the case of a wild type of GIF and that the molecular weight distribution shifted to the lower side (FIG. 2), indicating that the trimer structure was more unstable.

EXAMPLE 7

Biological Activity of Mammalian Cell-Derived Recombinant Mutant GIFS Whose Cysteine is Replaced by Serine

A. CONSTRUCTION AND EXPRESSION OF MUTANT GIFS IN MAMMALIAN CELLS

This coding sequences for cysteine residue (TGC) at position 57, 60 or 81 in SEQ ID NO: 1 were changed to those for serine residue (AGC), respectively, by using PCR. Two sets of PCR primers were employed to make one residue mutation. For the first set of primer, the sense primer corresponds the 5' coding sequences of human GIF with a ribosome binding site (ATC) and an additional EcoRI site at the upstream (primer A), and the anti-sense primer codes the sequences spanning the site for mutation (primer 1,2,3)

5'-GAATTCATCATGCCGATGTTCATCG-3' (primer A: SEQ ID NO:12)
3'-CTCGGCTCGCGCGAGACGTCGGACG-5' (primer 1: SEQ ID NO: 13)
3'-CTCGGCACGCGCGAGTCGTCGGACG-5' (primer 2: SEQ ID NO: 14)
3'-TCGACGACTCGCCGGACGACCGGCT-5' (primer 3: SEQ ID NO:15)

For the second set of primers, the sense primer codes the sequences spanning the site for mutation, overlapping the anti-sense primer of the first primer set (primer 4,5,6), and the anti-sense primer codes the 3' coding sequences of human GIF (primer B), with a stop codon (TAA) and an additional EcoRI site at the downstream.

5'-GAGCCGAGCGCGCTCTGCAGCCTGC-3' (primer 4: SEQ ID NO:16)
5'-GAGCCGTGCGCGCTCAGCAGCCTGC-3' (primer 5: SEQ ID NO: 17)
5'-AGCTGCTGAGCGGCCTGCTGGCCGA-3' (primer 6: SEQ ID NO:18)
3'-TTGAGGTGGAAGCGGATTCTTAAG-5' (primer B: SEQ ID NO: 19)

By using human GIFcDNA as template, each of the two cDNA fragments were amplified by PCR, and were then purified by using a Bio-Rad kit. Because of the overlapping sequences in the two cDNA fragments, the two fragments were then annealed and used as the template for the second round PCR, with the primers A and B as the primers to generate the mutated, full-length human GIF. For the generation of C57S-GIF whose cysteine residue at position 57 is replaced with serine residue, primers A, 1, 4 and B were used. For C60S-GIF whose cysteine residue at position 60 is replaced with serine residue, primers A, 2, 5 and B were used. For C81S-GIF whose cysteine residue at position 81 is replaced with serine residue, primers A, 3, 6 and B were used. The mutated cDNA fragment was then ligated to TA cloning vector (Invitrogen) and the sequence was verified by DNA sequencing. An EcoRI fragment encoding the human GIF with one residue mutation was then inserted to a mammalian expression vector, pEFneo (Liu, et al., *Proc. Natl. Acad Sci. USA*, 91: 11227, 1994) at the EcoRI site. The resulting plasmid was then transfected into BMT10 cells and the stable transfectants were selected by G418 resistance.

Culture supernatant of a selected transfectant was recovered, concerned, and absorbed either with anti-GIF polyclonal antibody-coupled affigel or with anti-GIF monoclonal antibody 388F1-coupled affigel (WO94/26923, supra). Proteins retained in the immunosorbent were eluted at acid pH, and concentration of GIF in the eluate fraction was determined by SDS-PAGE and silver staining.

B. BIOLOGICAL ACTIVITY OF MUTANT GIFS

GIF activity was detected by using T cell hybridoma 12H5 cells (Iwata, et al., *J. Immunol.*, 140: 2534, 1988). A suspension of the hybridoma cells was mixed with an equal volume of a test sample, and the cell suspensions were cultured for 24 hours with 10 μg/ml mouse IgE. Culture supernatants were filtered through CF50A membranes, and filtrates containing IgE-Binding Factor (IgE-BF) were fractionated on lentil-lectin Sepharose (Yodoi et al., *J. Immunol.*, 125: 1436, 1980). Both unbound proteins (effluent fraction) and those eluted with 0.2Mα methylmannoside (eluate fraction) were assessed for the presence of IGE-BF by rosette inhibition technique. If a sufficient amount of GIF were added to the culture of 12H5 cells together with mouse IgE, the majority of IGE-BF formed by the cells lacked affinity for lenti lectin and were recovered in the effluent fraction (Iwata & Ishizaka, *J. Immunol.*, 141: 3270, 1988). Thus, GIF was taken as (+), if the ratio of the percent rosette inhibition between the effluent/eluate fraction were 3.0 or higher. Minimum concentration required for the GIF activity is shown in TABLE 4.

TABLE 4

ACTIVITY OF GIF DERIVATIVES EXPRESSED IN BMT10 CELLS

| Sample | Minimum Concentration Required for GIF Activity | |
|---|---|---|
| Wild type (polyclonal anti-GIF purified) | >1000 | ng/ml |
| C57S | 62.5 | ng/ml |
| (Polyclonal Ab-purified) | 33.0 | ng/ml |
| (388F1-purified) | | |
| C60S | 500 | ng/ml |
| (Polyclonal Ab-purified) | | |
| CS1S | >500 | ng/ml |
| (Polyclonal Ab-purified) | | |

EXAMPLE 8

Preparation and Biological Activity of Modified E. Coli-Derived Recombinant GIF This example relates to the preparation of recombinant GIF derivatives in which a cysteine residue or residues were modified.

A. PREPARATION OF CARBOXYMETHYLATED RECOMBINANT GIF

Figure 3:
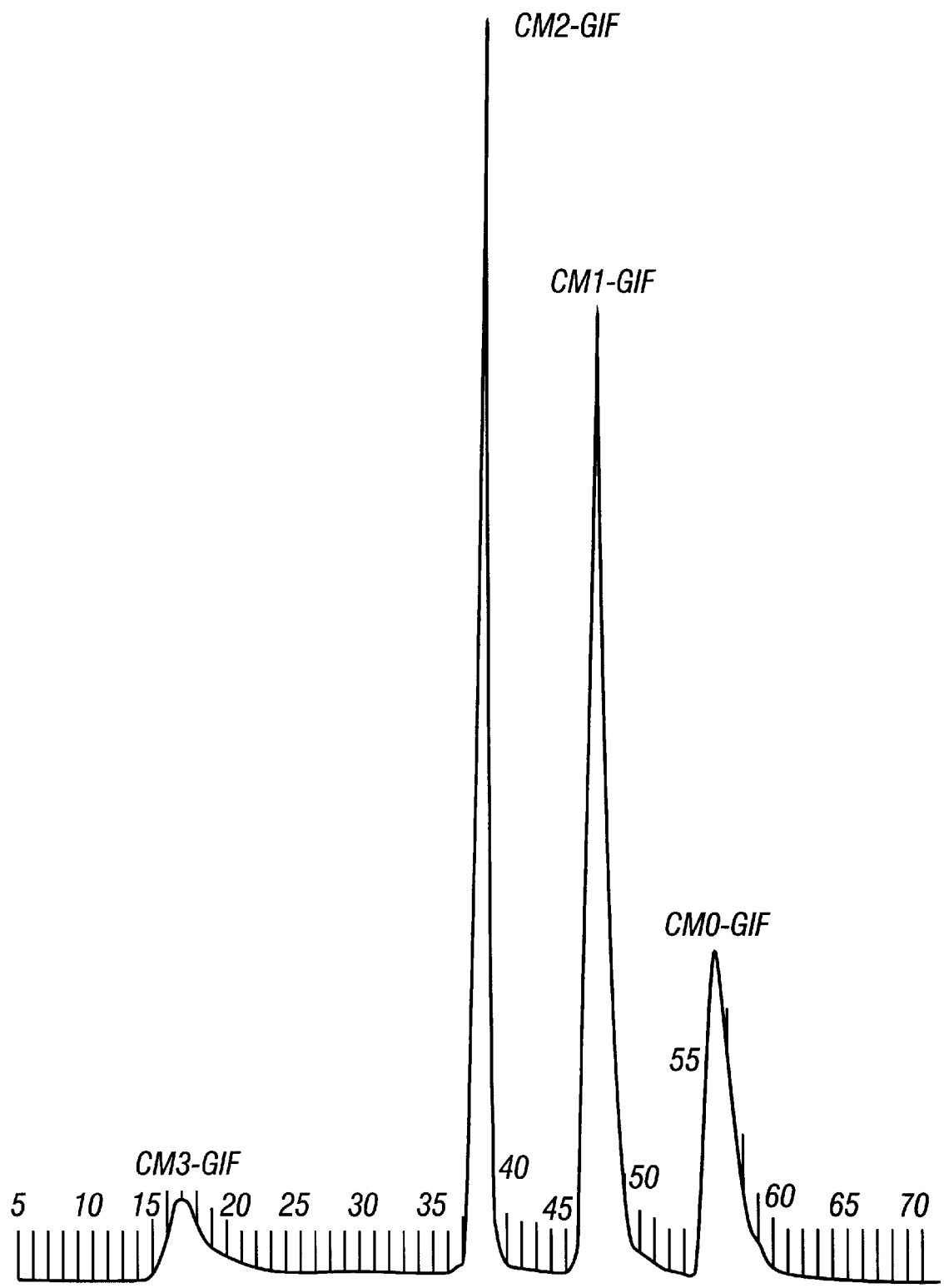
FIG. 3 shows a fractionation pattern of carboxymethylated recombinant GIF in a CM-5PW column.

The recombinant GIF (2.5 mg) containing the amino acid sequence of wild type which was used as a comparative control in Example 3 was dissolved in 1.25 ml of PBS. To the resulting solution was added 20 μl of monoiodoacetic acid dissolved in 1N sodium hydroxide at a concentration of 240 mg/ml and the mixture was left to stand overnight at room temperature. After the end of the reaction, the solvent was replaced with 20 mM sodium acetate buffer (pH 5.5) by using NAP-25 (Pharmacia) and the resulting solution was applied to TOSOH CM-5PW column (0.75×7.5 cm) equilibrated with the same buffer. The concentration of NaCl was increased linearly to 0.5M at a flow rate of 1.0 ml/min to elute proteins. The fractionation pattern indicated four peaks of the GIF derivative proteins (FIG. 3). The unreacted recombinant GIF produced a single peak in the same fraction as the fourth peak of the reacted GIF. The numbers of free SH groups of the GIF derivatives in the fractions of the first to fourth peaks were determined by Ellman's method (Glazer, et al., supra) to be 2.1, 2.4, 2.7 and 3.0, respectively. The results indicate that the first peak corresponds to a trimer of three GIF molecules in which one cysteine residue is alkylated; the second peak, a trimer of two GIF molecules in which one cysteine residue is alkylated and one GIF molecule in which no cysteine residue is alkylated; the third peak, a trimer of one GIF molecule in which one cysteine residue is alkylated and two GIF molecules in which no cysteine residue is alkylated; and the fourth peak, a trimer of three GIF molecules in which no cysteine residue is alkylated. The GIF molecules of the first to fourth peaks were denominated CM3-GIF, CM2-GIF, CM1-GIF and CM0-GIF, respectively.

The results of peptide mapping conducted as described in Example 4 revealed that the cysteine residue was modified only at the 60 position with monoiodoacetic acid.

B. BIOLOGICAL ACTIVITY OF CARBOXYMETHYLATED RECOMBINANT GIF

CM3-GIF, CM2-GIF, CM1-GIF and CM0-GIF were assayed for their in vivo antibody formation-inhibiting activity by the same method as in Example 3. As a result, activity levels varied depending on the modification levels of cysteine residues (Table 5).

TABLE 5

ACTIVITY OF MODIFIED RECOMBINANT GIF

| Sample | N | Anti DNP-IgG1 (μg/ml) |
|---|---|---|
| PBS (Control) | 10 | 35.3 ± 3.21 |
| CM0-GIF | 4 | 19.8 ± 5.54 |
| CM1-GIF | 4 | 14.9 ± 4.86 |
| CM2-GIF | 4 | 9.5 ± 0.97 |
| CM3-GIF | 4 | 30.1 ± 4.92 |

C. PREPARATION OF PYRIDYLETHYLATED RECOMBINANT GIF

Figure 4:
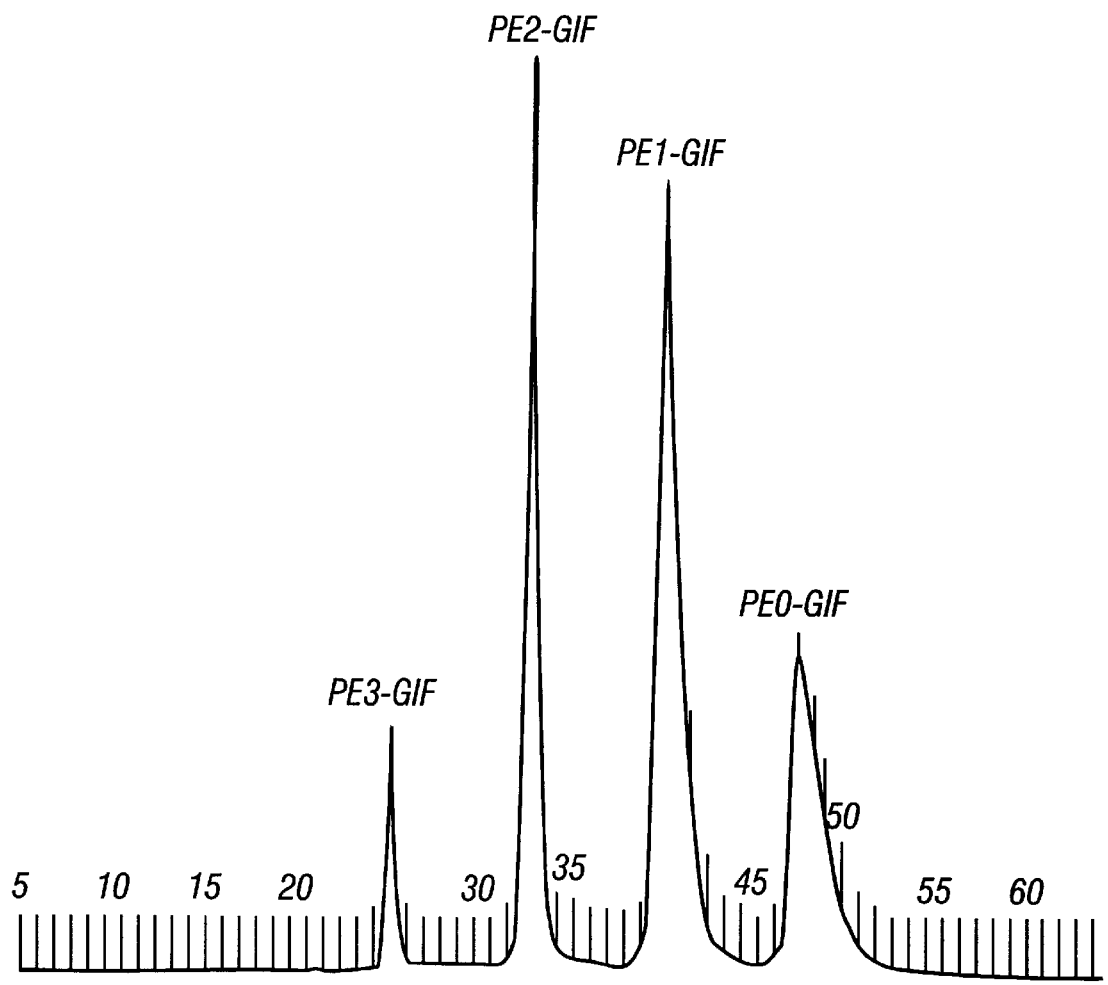
FIG. 4 shows a fractionation pattern of pyridylethylated recombinant GIF in a CM-5PW column.

The recombinant GIF (2.5 mg) containing the amino acid sequence of wild type which was used as a comparative control in Example 3 was dissolved in 1.25 ml of PBS. To the resulting solution was added 0.2 μl of 4-vinylpyridine and the mixture was left to stand overnight at room temperature. After the end of the reaction, the solvent was replaced with 20 mM sodium acetate buffer (pH 5.5) and the resulting solution was fractionated by using TOSOH CM-5PW column. The fractionation pattern contained four peaks of the GIF derivative proteins (FIG. 4) as in the case of carboxymethylation. The numbers of free SH groups of the GIF derivatives in the fractions of the first to fourth peaks were determined by Ellman's method to be 2.1, 2.4, 2.7 and 3.0, respectively. The GIF molecules of the first to fourth peaks were denominated PE3-GIF, PE2-GIF, PE1-GIF and PE0-GIF, respectively. As in the case of carboxymethylation, the cysteine residue was pyridylethylated only at the 60 position.

D. BIOLOGICAL ACTIVITY OF PYRIDYLETHYLATED RECOMBINANT GIF

PE3-GIF, PE2-GIF, PE1-GIF and PE0-GIF were assayed for their in vivo antibody formation-inhibiting activity by the same method as in Example 3. The results were not completely consistent with those of the carboxymethylated GIF. This inconsistency is believed to be due to the difference in chemical properties of the modifying groups. A raised level of activity was observed for all the modified GIFs (Table 6).

TABLE 6

ACTIVITY OF MODIFIED RECOMBINANT GIF

| Sample | N | Anti DNP-IgG1 (μg/ml) |
|---|---|---|
| PBS (Control) | 10 | 35.3 ± 3.21 |
| PE0-GIF | 4 | 25.5 ± 7.90 |
| PE1-GIF | 4 | 24.5 ± 5.67 |
| PE2-GIF | 4 | 21.3 ± 3.71 |
| PE3-GIF | 4 | 13.2 ± 2.09 |

EXAMPLE 9

Antiallergic Action of Recombinant GIF Derivatives

This example shows that the recombinant GIF derivatives are potent in their ability to inhibit an allergic reaction. C57A/N106S-GIF was examined for inhibition of an allergic reaction induced by immunization. BDF1 mice were immunized by an injection of 0.1 μg DNP-ovalbumin (OVA) absorbed to 1 mg of alum. C57A/N106S-GIF (20 μg) was injected i.p. the day before immunization and on days 0, 1, 2, 3, 4, 6, 8, 10 and 12. The control mice received PBS alone.

Fourteen days after immunization, 0.1 μg of DNP-BSA was injected into the ears of the mice and 0.25 ml of 0.5% Evans blue solution was injected i.v. The mice were sacrificed after 30 minutes and their ears were excised. The excised ears were immersed in 0.7 ml of 1N potassium hydroxide solution and incubated overnight at 37° C. To the incubated solution was added 9.3 ml of a mixed solution of 0.6N phosphoric acid and acetone (5:13) and the mixture was stirred. The amount of the dye in the supernatant was determined by measuring the absorbance at a wavelength of 620 nm. The comparative control mice received 1 mg/kg of antiallergic agent ketotifen on day 13. The experiment was repeated 2 times (Exps. 1 and 2).

Figure 5A:
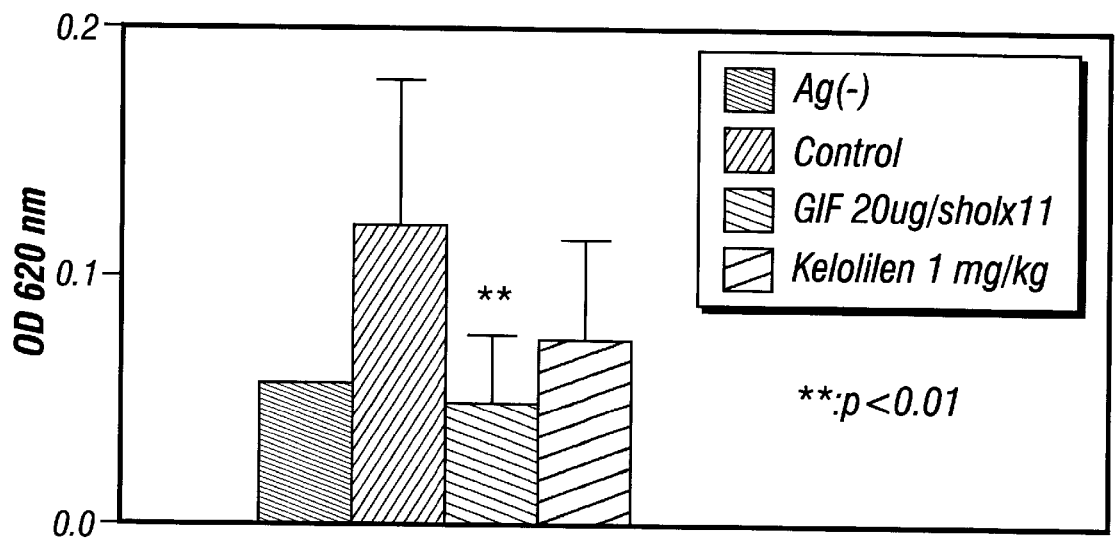
FIG. 5 shows the effect of a GIF derivative (C57A/N106S-GIF) on an allergic reaction (Active Cutaneous Anaphylaxis).
Figure 5B:
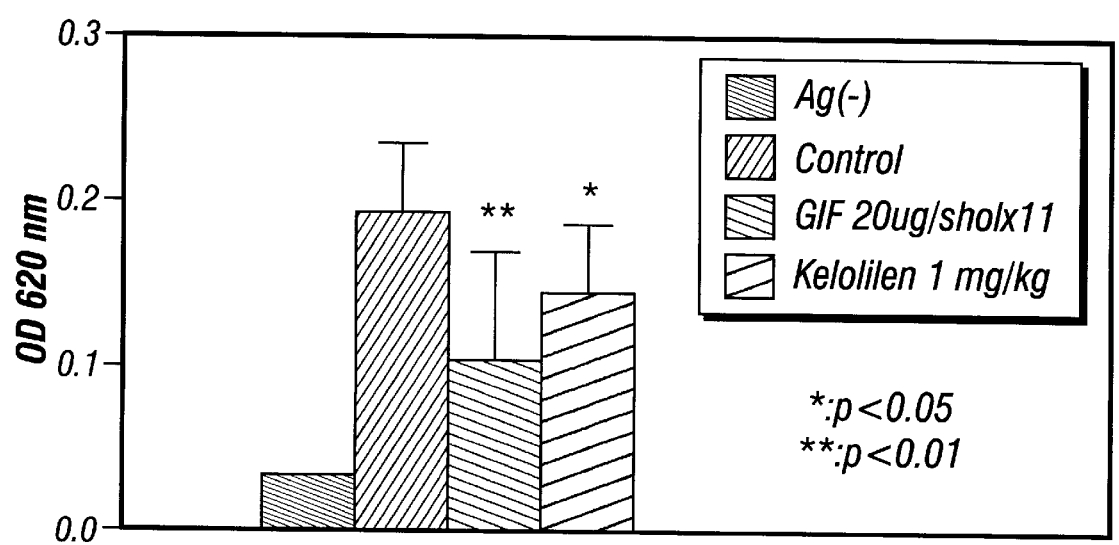

The results show that the C57A/N106S-GIF received mice exhibited little dye leakage, indicating that C57A/N106S-GIF had a higher antiallergic activity than commercially available antiallergic agent ketotifen (FIG. 5).

EXAMPLE 10

Preparation and Biological Activity of Modified E. Coli-Derived GIF Derivatives

A. PREPARATION OF CARBOXYMETHYLATED RECOMBINANT GIF DERIVATIVES

The recombinant GIF derivative (C57A or C57A/N106S) (0.2 mg) was dissolved in 10 ml of PBS, 5 μl of monoiodoacetic acid dissolved in 1N sodium hydroxide at a concentration of 240 mg/ml was added to the GIF derivative solution and the mixture was left to stand overnight at room temperature. After the end of the reaction, the solvent was concentrated to 1 ml by using YM3 membrane (Amicon). The resulting solution was added 50 ml of 20 mM sodium acetate buffer (pH 5.5) and concentrated to 1 ml again. This step was repeated one more time and the resulting solution was applied to TOSOH CM-5PW column (0.75×7.0 cm) equilibrated with 20 mM sodium acetate (pH 5.5). The concentration of NaCl was increased linearly to 0.5M at a flow rate of 1.0 ml/min to elute proteins. The first peak corresponds to a trimer of three GIF mutant molecules (C57A or C57A/N106S) in which one cysteine residue is alkylated was collected and denominated C57A-CM3 or C57A/N106S-CM, respectively.

The results of peptide mapping conducted as described in Example 4 revealed that the cysteine residue was modified at the 60 position and/or at the 81 position with a carboxymethyl group.

B. BIOLOGICAL ACTIVITY OF CARBOXYMETHYLATED RECOMBINANT GIF DERIVATIVES

C57A-CM3 and C57A/N106S-CM were assayed for their in vivo antibody formation-inhibiting activity by the similar method as in Example 3 except three times of administration on days -1, 0 and 1 instead of 9 times injection. As a result, carboxymethylated GIF derivatives showed higher activity than C57A or C57A/N106S (Table 7). In vitro assay of the same preparations for the detection of bioactivity (see Example 3), shown in Table 7, also indicated that carboxymethylation of C57A and C57A/N106 markedly enhanced the activity.

TABLE 7

ACTIVITY OF MODIFIED GIF DERIVATIVES

| Sample | N | Anti DNP-IgE(ng/ml) | Minimum Concentration for invitro GIF activity (ng/ml) |
|---|---|---|---|
| PBS (Control) | 6 | 2684.1 ± 675.9 | — |
| C57A | 4 | 1750.2 ± 491.5 | 100 |
| C57A-CM3 | 4 | 200.2 ± 52.5 | 10 |
| C57A/N106S | 4 | 397.2 ± 214.0 | 100 |
| C57A/N106S-CM | 4 | 126.5 ± 48.9 | 10 |

EXAMPLE 11

Prevention of Spontaneous Diabetes in NOD Mice by Recombinant GIF Derivatives This example shows that the recombinant GIF derivatives are potent in their ability to prevent insulin-dependent diabetes mellitus.

Figure 6:
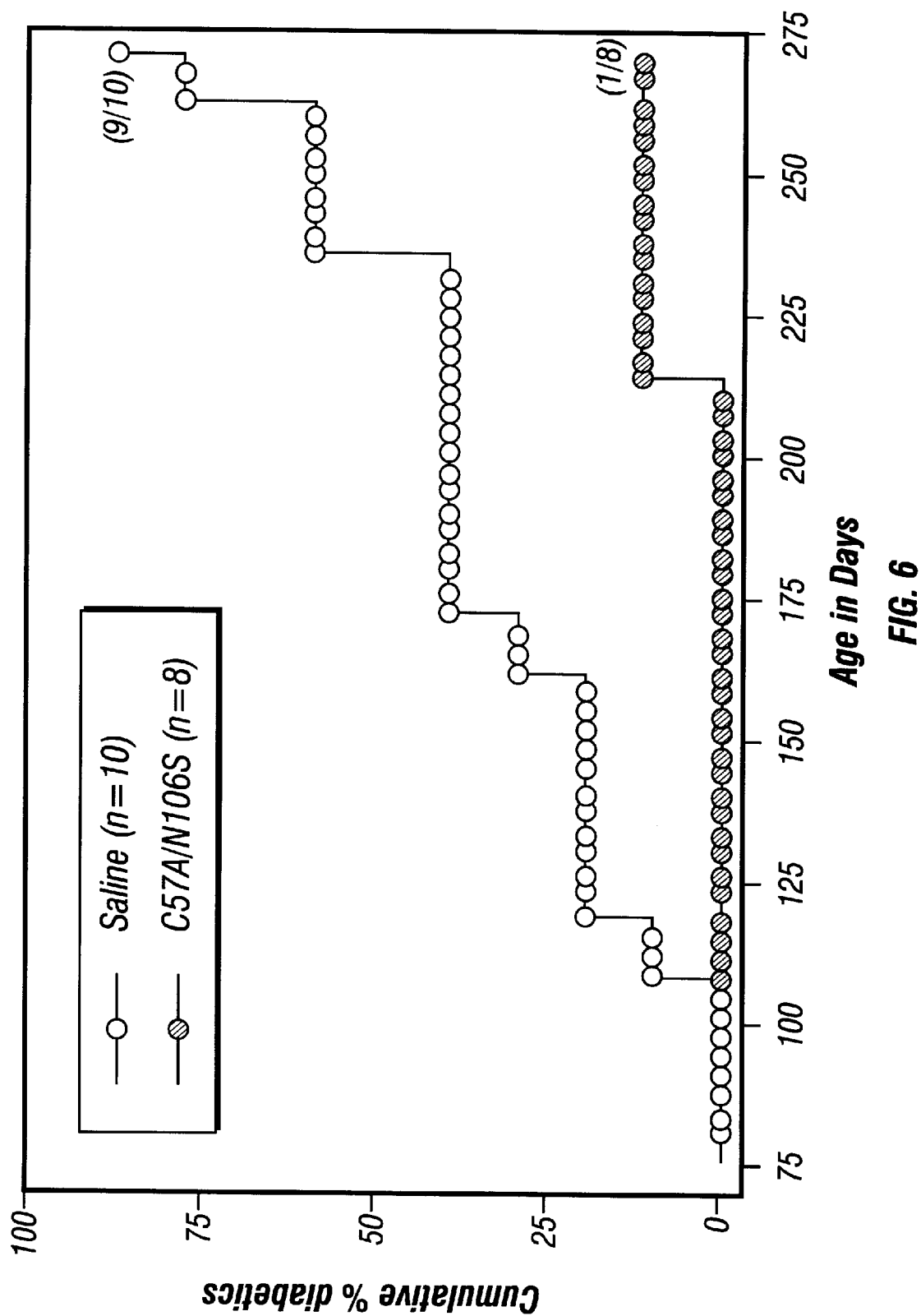
FIG. 6 shows the effect of a GIF derivative (C57A/N106S) on an development of insulin-dependent diabetes mellitus.

NOD (nonobese diabetic) female mice (Serreze, D. V. et al, J. of Autoimmunity, 2:759, 1989), Bowman, M. A. et al, Immunology Today, 15, No. 3, 115–120(1994)) were treated i.p. from 5 to 38 weeks of age with 10 μg of C57A/N106S three times/week. Mice were monitored for glycosuria once a week using test strips and a calorimetric assay. Diabetes was diagnosed when permanent fasting glucose levels above 200 mg/dl occurred. Almost complete protection against spontaneous diabetes was observed in mice treated with C57A/N106S (FIG. 6).

EXAMPLE 12

Preparation and Biological Activity of EMTS- or DTNB-Modified Recombinant GIF

A. PREPARATION OF EMTS-MODIFIED GIF

100 μg/ml of the recombinant wild type GIF which was used as a comparative control in Example 3 dissolved in PBS was incubated with various concentrations of ethylmercurithiosalicylate (EMTS) for 24 hr at 4° C. After extensive dialysis against PBS, the concentration of the derivatives was measured by ELISA, and bioactivity of the preparations was determined. In order to isolate EMTS-modified GIF, the sample was fractionated on a CM-5PW column equilibrated with 10 mM phosphate buffer (pH 6.5). The concentration of NaCl was increased linearly to 0.5M at a flow rate of 0.5 ml/min to elute proteins, and two major peaks were obtained. Comparisons of the elution profile with that of untreated GIF from the same column indicated that the latter protein peak, recovered at 36–38 min., corresponded to unmodified GIF, while the former peak, recovered at 31–34 min., did not exist in the original GIF preparation.

B. BIOLOGICAL ACTIVITY OF EMTS-MODIFIED RECOMBINANT GIF

The GIF bioactivity of the EMTS-treated GIF and the fractionated GIF was assessed by the ability to switch the murine T cell hybridoma 12H5 cells from the formation of glycosylated IgE-binding factor to the formation of unglycosylated IgE-binding factor as described in Example 3. The minimum concentration of the GIF derivative for the detection of the GIF bioactivity is shown in Table 8.

TABLE 8

ACTIVITY OF EMTS-MODIFIED GIF

| EMTS concentration(mM) | CM-5W franctionation | Minimum concentration for bioactivity(ng/ml) |
|---|---|---|
| Untreated | unfractioned | >1000 |
| 0.05 | unfractionated | 10 |
| 0.25 | unfractionated | 5 |
| 0.25 | former peak | 2 |
| 0.25 | latter peak | 500 |

The results clearly show that the protein in the former peak represents the bioactive derivative of GIF. To confirm that the generation of bioactive GIF is due to modification of a sulfhydryl group(s), a portion of the bioactive GIF derivative, which was prepared by the treatment with EMTS, was incubated overnight with 5 mM dithiothreitol at 4° C. Measurement of the GIF bioactivity of the reduced material, after extensive dialysis, showed that 1 $\mu$g/ml of the reduced form GIF was required for the detection of GIF bioactivity, indicating that the effect of EMTS treatment on GIF bioactivity is due to the reaction of EMTS with cysteine residue(s).

C. PREPARATION OF DTNB-MODIFIED GIF

In order to avoid the possibility that the generation of a highly bioactive derivative is unique for mercaptide formation of SH group, recombinant wild type GIF was treated with another thiol reagent 5,5'-dithiobis(2-nitrobenzoic acid) (DTNB). A solution of 130 $\mu$g/ml GIF in PBS was incubated for 24 hr with various concentrations of DTNB at 4° C., and dialyzed extensively against PBS. The resulting DTNB-treated GIF was further fractionated on a CM-5PW column as described in A. Chromatogram showed one major peak recovered between 26 and 29 min., indicating that unmodified GIF which was eluted at 46–48 min under the experimental conditions, was undetectable.

D. BIOLOGICAL ACTIVITY OF DTNB-MODIFIED RECOMBINANT GIF

The GIF bioactivity of DTNB-modified GIF derivatives was measured by the methods as described in B and shown in Table 9.

TABLE 9

ACTIVITY OF DTNB-MODIFIED GIF

| ZDTNB concentration(mM) | CM-5PW fractionation | Minimum concentration for bioactivity(ng/ml) |
|---|---|---|
| untreated | unfractionated | >1000 |
| 0.10 | unfractionated | 10 |
| 0.25 | unfractionated | 8 |
| 0.25 | major peak | 5 |

The results indicate that incorporation of mercury is not essential for the generation of highly bioactive GIF.

A portion of the bioactive GIF derivative was incubated overnight with 5 mM dithiothreitol at 4° C., and then extensively dialyzed. Determination of the GIF bioactivity indicated that even 1 $\mu$g/ml reduced from GIF failed to show GIF activity. The results indicated that modification of SH group(s) in inactive rGIF with DTNB resulted in the generation of high GIF bioactivity.

Pharmaceutical preparation examples will now be described.

Preparation Example 1

A solution containing C57A-GIF which was obtained in Example 2 was filtered aseptically and charged in a 10 ml vial to prepare an injection.

Preparation Example 2

A solution containing C57A-GIF which was obtained in Example 2 was filtered aseptically and concentrated, followed by charging 5 ml of the concentrated solution in a 10 ml vial under aseptic conditions. After lyophilization at −20° C., the vial containing the lyophilized product was plugged with a rubber stopper to prepare an injection.

Preparation Example 3

A solution containing C57/AN106S-GIF which was obtained in Example 6 was filtered aseptically and charged in a 10 ml vial to prepare an injection.

Preparation Example 4

A solution containing C57A/N106S-GIF which was obtained in Example 6 was filtered aseptically and concentrated, followed by charging 5 ml of the concentrated solution in a 10 ml vial under aseptic conditions. After lyophilization at −20° C., the vial containing the lyophilized product was plugged with a rubber stopper to prepare an injection.

Preparation Example 5

A solution containing CM2-GIF which was obtained in Example 8 was filtered aseptically and charged in a 10 ml vial to prepare an injection.

Preparation Example 6

A solution containing CM2-GIF which was obtained in Example 8 was filtered aseptically and concentrated, followed by charging 5 ml of the concentrated solution in a 10 ml vial under aseptic conditions. After lyophilization at −20° C., the vial containing the lyophilized product was plugged with a rubber stopper to prepare an injection.

Preparation Example 7

A solution containing PE3-GIF which was obtained in Example 8 was filtered aseptically and charged in a 10 ml vial to prepare an injection.

Preparation Example 8

A solution containing PE3-GIF which was obtained in Example 8 was filtered aseptically and concentrated, followed by charging 5 ml of the concentrated solution in a 10 ml vial under aseptic conditions. After lyophilization at −20° C., the vial containing the lyophilized product was plugged with a rubber stopper to prepare an injection.

Preparation Example 9

A solution containing C57S-GIF which was obtained in Example 7 was filtered aseptically and charged in a 10 ml vial to prepare an injection.

Preparation Example 10

A solution containing C57S-GIF which was obtained in Example 7 was filtered aseptically and concentrated, followed by charging 5 ml of the concentrated solution in a 10 ml vial under aseptic conditions. After lyophilization at −20° C., the vial containing the lyophilized product was plugged with a rubber stopper to prepare an injection.

Preparation Example 11

A solution containing C57A-CM3 which was obtained in Example 10 was filtered aseptically and charged in a 10 ml vial to prepare an injection.

Preparation Example 12

A solution containing C57A-CM3 which was obtained in Example 10 was filtered aseptically and concentrated, followed by charging 5 ml of the concentrated solution in a 10 ml vial under aseptic conditions. After lyophilization at −20° C., the vial containing the lyophilized product was plugged with a rubber stopper to prepare an injection.

Preparation Example 13

A solution containing C57A/N106S-CM which was obtained in Example 10 was filtered aseptically and charged in a 10 ml vial to prepare an injection.

Preparation Example 14

A solution containing C57A/N106S-CM which was obtained in Example 10 was filtered aseptically and concentrated, followed by charging 5 ml of the concentrated solution in a 10 ml vial under aseptic conditions. After lyophilization at −20° C., the vial containing the lyophilized product was plugged with a rubber stopper to prepare an injection.

Preparation Example 15

A solution containing the EMTS-modified GIF (the former peak in the CM-5PW fractionation) which was obtained in Example 12A was filtered aseptically and charged in a 10 ml vial to prepare an injection.

Preparation Example 16

A solution containing the EMTS-modified GIF (the former peak in the CM-5PW fractionation) which was obtained in Example 12 was filtered aseptically and concentrated, followed by charging 5 ml of the concentrated solution in a 10 ml vial under aseptic conditions. After lyophilization at −20° C., the vial containing the lyophilized product was plugged with a rubber stopper to prepare an injection.

Preparation Example 17

A solution containing the DTNB-modified GIF (the major peak in the CM-5PW fractionation) which was obtained in Example 12C was filtered aseptically and charged in a 10 ml vial to prepare an injection.

Preparation Example 18

A solution containing the DTNB-modified GIF (the major peak in the CM-5PW fractionation) which was obtained in Example 12C was filtered aseptically and concentrated, followed by charging 5 ml of the concentrated solution in a 10 ml vial under aseptic conditions. After lyophilization at −20° C., the vial containing the lyophilized product was plugged with a rubber stopper to prepare an injection.

While the preferred embodiments of the invention have been described above, it is to be understood that various changes and modifications will be apparent to those skilled in the art without departing from the spirit of the invention.

The scope of the invention, therefore, is to be determined solely by the following claims.

---

We claim:

1. An antigen non-specific glycosylation inhibiting factor (GIF) derivative, wherein said GIF comprises the amino acid sequence set forth in SEQ ID NO:21, wherein said derivative differs from said GIF by the replacement, deletion, substitution, or chemical modification of amino acid(s) 57 and/or 60 of SEQ ID NO:21, wherein said derivative may be further modified by the replacement, deletion, substitution, or chemical modification of at least one amino acid in the amino acid sequence selected from the group consisting of amino acids 37–45, 47–50, 59, 94–98 and 106–110 of SEQ ID NO:21, wherein the amino acid at position number 1 of SEQ ID NO:21 may be deleted and wherein said derivative has GIF immunosuppressive activity.

2. The antigen non-specific human glycosylation inhibiting factor derivative of claim 1, wherein the amino acid at position 57 of SEQ ID NO:21 is replaced, deleted, or substituted and said further modification is introduced in at least one of said amino acids and wherein said further chemical modification is selected from the group consisting of phosphorylation, alkylation, ethylmercurithiosalicylate (EMTS)-modification and 5,5'-dithiobis(-2-nitrobenzoic acid) (DNTB)-modification.

3. The antigen non-specific glycosylation inhibiting factor derivative of claim 2, wherein the cysteine residue is replaced with an alanine or a serine residue at the 57 position of SEQ ID NO:21.

4. The antigen non-specific human glycosylation inhibiting factor derivative of claim 2, wherein a cysteine residue is carboxymethylated.

5. The antigen non-specific human glycosylation inhibiting factor derivative of claim 2, wherein said further modification is introduced in the asparagine residue at the 106 position of SEQ ID NO:21.

6. The antigen non-specific human glycosylation inhibiting factor derivative of claim 5, wherein said asparagine residue is replaced with a serine residue.

7. A pharmaceutical composition comprising the antigen non-specific human glycosylation inhibiting factor derivative of claim 1, and a pharmaceutically acceptable carrier.

8. A method of suppressing a human immune response to an antigen which comprises administering to the human an immunosuppressively effective amount of the antigen non-specific human glycosylation inhibiting factor derivative of claim 1.

9. The method of claim 8, wherein said derivative differs from said GIF by the replacement, deletion, substitution or chemical modification of amino acid(s) 57 and/or 60 of SEQ ID NO:21.

10. The method of claim 8, wherein the administration is parenteral.

11. The method of claim 10, wherein the parenteral administration is by subcutaneous, intramuscular, intraperitoneal, intracavity, transdermal, or intravenous injection.

12. The method of claim 8, which is used for the treatment of diabetes.

13. The antigen non-specific human glycosylation inhibiting factor derivative of claim 1, wherein the cysteine residue at the 57 position of SEQ ID NO:21 is replaced with an alanine or a serine residue.

14. The antigen non-specific human glycosylation inhibiting factor derivative of claim 1, wherein the cysteine residue at the 57 position of SEQ ID NO:21 is replaced with an alanine residue and the asparagine residue at the 106 position of SEQ ID NO:21 is replaced with a serine residue.

15. The antigen non-specific human glycosylation inhibiting factor derivative of claim 1, wherein said chemical modifications are selected from the group consisting of phosphorylation, alkylation, acylation, and chemical modification with either ethylmercurithiosalicylate (EMTS) or 5,5'-dithiobis(-2-nitrobenzoic acid) (DNTB).

16. The antigen non-specific human glycosylation inhibiting factor derivative of claim 15, wherein said chemical modifications are carboxymethylation.

17. The antigen non-specific human glycosylation inhibiting factor derivative of claim 15, wherein said chemical modifications are pyridylethylation.

18. A polynucleotide encoding an antigen non-specific glycosylation inhibiting factor (GIF) derivative, wherein said GIF comprises the amino acid sequence set forth in SEQ ID NO:21, wherein said derivative differs from said GIF by the replacement, deletion, or substitution of amino acid(s) 57 and/or 60 of SEQ ID NO:21, wherein said derivative may be further modified by the replacement, deletion, or substitution of at least one amino acid in the amino acid sequence selected from the group consisting of amino acids 37–45, 47–50, 59, 94–98 and 106–110 of SEQ ID NO:21, wherein the amino acid at position number 1 of SEQ ID NO:21 may be deleted and wherein said derivative has GIF immunosuppressive activity.

19. A recombinant vector containing the polynucleotide of claim 18.

20. A prokaryotic or eukaryotic cell transformed with the polynucleotide of claim 18.

21. The cell of claim 20, wherein the prokaryotic cell is a bacterium.

22. The cell of claim 20, wherein the prokaryotic cell is *E. coli*

23. The cell of claim 20, wherein the eukaryotic cell is a mammalian cell.

24. A method of producing an antigen non-specific human glycosylation inhibiting factor derivative comprising culturing the prokaryotic or eukaryotic cell of claim 20 and isolating and purifying the produced antigen non-specific human glycosylation inhibiting factor derivative.

25. The polynucleotide of claim 18, wherein the codon encoding a cysteine residue at position 57 of SEQ ID NO:21 is replaced with a codon encoding an alanine or a serine residue.

26. The polynucleotide of claim 18, wherein the codon encoding a cysteine residue at position 57 of SEQ ID NO:21 is replaced with a codon encoding an alanine residue and the codon encoding an asparagine residue is replaced with a codon encoding a serine residue at position 106 of SEQ ID NO:21.

27. A method of producing an antigen non-specific human glycosylation inhibiting factor (GIF) derivative, comprising chemically modifying at least one amino acid selected from the group consisting of amino acids 57 and 60 of SEQ ID NO:21, wherein said derivative has GIF immunosuppressive activity.

28. The method of claim 27, wherein the chemical modification is selected from the group consisting of phosphorylation, alkylation, acylation, ethylmercurithiosalicylate (EMTS)-modification and 5,5'-dithiobis(-2-nitrobenzoic acid) (DNTB)-modification.

* * * * *

UNITED STATES PATENT AND TRADEMARK OFFICE
CERTIFICATE OF CORRECTION

PATENT NO. : 5,910,427
DATED : 06/08/99
INVENTOR(S) : Mikayama et al.

It is certified that error appears in the above-identified patent and that said Letters Patent is hereby corrected as shown below:

In column 37, line 43, claim 2, please delete "ethlymercurithiosalicylate" and replace with --ethylmercurithiosalicylate--.

In column 37, line 62, claim 7, after "claim 1", please delete ",".

Signed and Sealed this

Twenty-ninth Day of February, 2000

*Attest:*

*Attesting Officer*

Q. TODD DICKINSON

*Commissioner of Patents and Trademarks*

UNITED STATES PATENT AND TRADEMARK OFFICE
CERTIFICATE OF CORRECTION

PATENT NO. : 5,910,427
DATED : June 8, 1999
INVENTOR(S) : Mikayama et al.

It is certified that error appears in the above-identified patent and that said Letters Patent is hereby corrected as shown below:

<u>Title page,</u>
Item [73], after "La Jolla Institute for Allergy and Immunology, La Jolla, Calif." please insert -- Kirin Beer Kabushiki Kaisha, 10-1, Shinkawa 2-Chome, Chuo-Ku, Tokyo, Japan 104 --

Signed and Sealed this

Second Day of April, 2002

*Attest:*

*Attesting Officer*

JAMES E. ROGAN
*Director of the United States Patent and Trademark Office*

SEQUENCE LISTING

```
(1) GENERAL INFORMATION:

(iii) NUMBER OF SEQUENCES: 21

(2) INFORMATION FOR SEQ ID NO:1:

(i) SEQUENCE CHARACTERISTICS:
        (A) LENGTH: 348 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Homo sapiens
        (H) CELL LINE: Suppressor T-cell hybridoma AC5
        (Accession No. HB 10473)

(ix) FEATURE:
        (A) NAME/KEY: CDS
        (B) LOCATION: 1..346

(xi) SEQUENCE DESCRIPTION: SEQ ID NO:1:

ATG CCG ATG TTC ATC GTA AAC ACC AAC GTG CCC CGC GCC TCC GTG CCG        48
Met Pro Met Phe Ile Val Asn Thr Asn Val Pro Arg Ala Ser Val Pro
1               5                   10                  15

GAC GGG TTC CTC TCC GAG CTC ACC CAG CAG CTG GCG CAG GCC ACC GGC        96
Asp Gly Phe Leu Ser Glu Leu Thr Gln Gln Leu Ala Gln Ala Thr Gly
            20                  25                  30
```

```
AAG CCC CCC CAG TAC ATC GCG GTG CAC GTG GTC CCG GAC CAG CTC ATG         144
Lys Pro Pro Gln Tyr Ile Ala Val His Val Val Pro Asp Gln Leu Met
         35                  40                  45

GCC TTC GGC GGC TCC AGC GAG CCG TGC GCG CTC TGC AGC CTG CAC AGC         192
Ala Phe Gly Gly Ser Ser Glu Pro Cys Ala Leu Cys Ser Leu His Ser
 50                  55                  60

ATC GGC AAG ATC GGC GGC GCG CAG AAC CGC TCC TAC AGC AAG CTG CTG         240
Ile Gly Lys Ile Gly Gly Ala Gln Asn Arg Ser Tyr Ser Lys Leu Leu
 65                  70                  75                  80

TGC GGC CTG CTG GCC GAG CGC CTG CGC ATC AGC CCG GAC AGG GTC TAC         288
Cys Gly Leu Leu Ala Glu Arg Leu Arg Ile Ser Pro Asp Arg Val Tyr
                 85                  90                  95

ATC AAC TAT TAC GAC ATG AAC GCG GCC AAT GTG GGC TGG AAC AAC TCC         336
Ile Asn Tyr Tyr Asp Met Asn Ala Ala Asn Val Gly Trp Asn Asn Ser
                100                 105                 110

ACC TTC GCC   T AA                                                      348
Thr Phe Ala
        115

(2) INFORMATION FOR SEQ ID NO:2:

(i) SEQUENCE CHARACTERISTICS:
        (A) LENGTH: 348 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Synthetic DNA"

(ix) FEATURE:
        (A) NAME/KEY: CDS
        (B) LOCATION: 1..346

(xi) SEQUENCE DESCRIPTION: SEQ ID NO:2:

ATG CCG ATG TTC ATC GTA AAC ACC AAC GTG CCC CGC GCC TCC GTG CCG          48
Met Pro Met Phe Ile Val Asn Thr Asn Val Pro Arg Ala Ser Val Pro
                120                 125                 130

GAC GGG TTC CTC TCC GAG CTC ACC CAG CAG CTG GCG CAG GCC ACC GGC          96
Asp Gly Phe Leu Ser Glu Leu Thr Gln Gln Leu Ala Gln Ala Thr Gly
            135                 140                 145

AAG CCC CCC CAG TAC ATC GCG GTG CAC GTG GTC CCG GAC CAG CTC ATG         144
Lys Pro Pro Gln Tyr Ile Ala Val His Val Val Pro Asp Gln Leu Met
        150                 155                 160

GCC TTC GGC GGC TCC AGC GAG CCG GCC GCG CTC TGC AGC CTG CAC AGC         192
Ala Phe Gly Gly Ser Ser Glu Pro Ala Ala Leu Cys Ser Leu His Ser
165                 170                 175

ATC GGC AAG ATC GGC GGC GCG CAG AAC CGC TCC TAC AGC AAG CTG CTG         240
Ile Gly Lys Ile Gly Gly Ala Gln Asn Arg Ser Tyr Ser Lys Leu Leu
180                 185                 190                 195

TGC GGC CTG CTG GCC GAG CGC CTG CGC ATC AGC CCG GAC AGG GTC TAC         288
Cys Gly Leu Leu Ala Glu Arg Leu Arg Ile Ser Pro Asp Arg Val Tyr
                200                 205                 210

ATC AAC TAT TAC GAC ATG AAC GCG GCC AAT GTG GGC TGG AAC AAC TCC         336
Ile Asn Tyr Tyr Asp Met Asn Ala Ala Asn Val Gly Trp Asn Asn Ser
                215                 220                 225

ACC TTC GCC   T AA                                                      348
Thr Phe Ala
        230

(2) INFORMATION FOR SEQ ID NO:3:

(i) SEQUENCE CHARACTERISTICS:
        (A) LENGTH: 348 base pairs
        (B) TYPE: nucleic acid
```

```
        (C) STRANDEDNESS: double
        (D) TOPOLOGY: linear (ii) MOLECULE TYPE: other nucleic acid
        (A) DESCRIPTION: /desc = "Synthetic DNA"

(ix) FEATURE:
        (A) NAME/KEY: CDS
        (B) LOCATION: 1..346

(xi) SEQUENCE DESCRIPTION: SEQ ID NO:3:
```

| | | | | | | | | | | | | | | | | |
|---|---|---|---|---|---|---|---|---|---|---|---|---|---|---|---|---|
| ATG | CCG | ATG | TTC | ATC | GTA | AAT | ACC | AAC | GTG | CCC | CGA | GCC | TCC | GTG | CCG | 48 |
| Met | Pro | Met | Phe | Ile | Val | Asn | Thr | Asn | Val | Pro | Arg | Ala | Ser | Val | Pro | |
| | | | | 120 | | | | 125 | | | | | 130 | | | |
| GAC | GGG | TTC | CTC | TCC | GAG | CTC | ACC | CAG | CAG | CTG | GCG | CAG | GCC | ACC | GGC | 96 |
| Asp | Gly | Phe | Leu | Ser | Glu | Leu | Thr | Gln | Gln | Leu | Ala | Gln | Ala | Thr | Gly | |
| | | | 135 | | | | 140 | | | | 145 | | | | | |
| AAG | CCT | CCA | CAG | TAC | ATC | GCG | GTG | CAC | GTG | GTC | CCG | GAC | CAG | CTC | ATG | 144 |
| Lys | Pro | Pro | Gln | Tyr | Ile | Ala | Val | His | Val | Val | Pro | Asp | Gln | Leu | Met | |
| | | | 150 | | | | 155 | | | | 160 | | | | | |
| GCC | TTC | GGC | GGC | TCC | AGC | GAG | CCG | GCC | GCG | CTC | TGC | AGC | CTG | CAC | AGC | 192 |
| Ala | Phe | Gly | Gly | Ser | Ser | Glu | Pro | Ala | Ala | Leu | Cys | Ser | Leu | His | Ser | |
| | 165 | | | | 170 | | | | 175 | | | | | | | |
| ATC | GGC | AAG | ATC | GGC | GGC | GCG | CAG | AAC | CGC | TCC | TAC | AGC | AAG | CTG | CTG | 240 |
| Ile | Gly | Lys | Ile | Gly | Gly | Ala | Gln | Asn | Arg | Ser | Tyr | Ser | Lys | Leu | Leu | |
| 180 | | | | 185 | | | | 190 | | | | | 195 | | | |
| TGC | GGC | CTG | CTG | GCC | GAA | CGC | CTT | CGC | ATC | AGC | CCG | GAC | AGG | GTC | TAC | 288 |
| Cys | Gly | Leu | Leu | Ala | Glu | Arg | Leu | Arg | Ile | Ser | Pro | Asp | Arg | Val | Tyr | |
| | | | 200 | | | | 205 | | | | 210 | | | | | |
| ATC | AAC | TAT | TAC | GAC | ATG | AAC | GCG | GCT | AGC | GTG | GGC | TGG | AAC | AAC | TCC | 336 |
| Ile | Asn | Tyr | Tyr | Asp | Met | Asn | Ala | Ala | Ser | Val | Gly | Trp | Asn | Asn | Ser | |
| | | 215 | | | | 220 | | | | 225 | | | | | | |
| ACC | TTC | GCC | T | AA | | | | | | | | | | | | 348 |
| Thr | Phe | Ala | | | | | | | | | | | | | | |
| | 230 | | | | | | | | | | | | | | | |

```
(2) INFORMATION FOR SEQ ID NO:4:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:4:

AACCTTAAGA AAAACCAAGG AGGTAATAAA TAATGCCGAT GTTCATCGTA AACACCAACG        60

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:5:

CAGGCTGCAG AGCGCGGCCG GCTC                                               24
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:6:

GATGCTGTGC AGGCTAGCGA GCGC                                      24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:7:

GCGCTCGCTA GCCTGCACAG CATC                                      24

(2) INFORMATION FOR SEQ ID NO:8:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:8:

AACGGATCCC TATTAGGCGA AGGTGGAGTT GTTCCAGCCC AC                  42

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:9:

TTCGACGATC GGCCGGACGA CCGG                                      24

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:10:

AAGCTGCTAG CCGGCCTGCT GGCC                                      24

(2) INFORMATION FOR SEQ ID NO:11:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(ix) FEATURE:
        (A) NAME/KEY: CDS
        (B) LOCATION: 1..346

(xi) SEQUENCE DESCRIPTION: SEQ ID NO:11:

```
ATG CCG ATG TTC ATC GTA AAT ACC AAC GTG CCC CGA GCC TCC GTG CCG         48
Met Pro Met Phe Ile Val Asn Thr Asn Val Pro Arg Ala Ser Val Pro
             120                 125                 130

GAC GGG TTC CTC TCC GAG CTC ACC CAG CAG CTG GCG CAG GCC ACC GGC         96
Asp Gly Phe Leu Ser Glu Leu Thr Gln Gln Leu Ala Gln Ala Thr Gly
             135                 140                 145

AAG CCT CCA CAG TAC ATC GCG GTG CAC GTG GTC CCG GAC CAG CTC ATG        144
Lys Pro Pro Gln Tyr Ile Ala Val His Val Val Pro Asp Gln Leu Met
             150                 155                 160

GCC TTC GGC GGC TCC AGC GAG CCG TGC GCA CTC TGC AGC CTG CAC AGC        192
Ala Phe Gly Gly Ser Ser Glu Pro Cys Ala Leu Cys Ser Leu His Ser
             165                 170                 175

ATC GGC AAG ATC GGC GGC GCG CAG AAC CGC TCC TAC AGC AAG CTG CTG        240
Ile Gly Lys Ile Gly Gly Ala Gln Asn Arg Ser Tyr Ser Lys Leu Leu
180                  185                 190                 195

TGC GGC CTG CTG GCC GAA CGC CTT CGC ATC AGC CCG GAC AGG GTC TAC        288
Cys Gly Leu Leu Ala Glu Arg Leu Arg Ile Ser Pro Asp Arg Val Tyr
             200                 205                 210

ATC AAC TAT TAC GAC ATG AAC GCG GCT AGC GTG GGC TGG AAC AAC TCC        336
Ile Asn Tyr Tyr Asp Met Asn Ala Ala Ser Val Gly Trp Asn Asn Ser
             215                 220                 225

ACC TTC GCC  T AA                                                      348
Thr Phe Ala
       230
```

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:12:

GAATTCATCA TGCCGATGTT CATCG                                        25

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:13:

GCAGGCTGCA GAGCGCGCTC GGCTC                                        25

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:14:

GCAGGCTGCT GAGCGCGCAC GGCTC                                                25

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:15:

TCGGCCAGCA GGCCGCTCAG CAGCT                                                25

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:16:

GAGCCGAGCG CGCTCTGCAG CCTGC                                                25

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:17:

GAGCCGTGCG CGCTCAGCAG CCTGC                                                25

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:18:

AGCTGCTGAG CGGCCTGCTG GCCGA                                                25

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:19:

```
GAATTCTTAG GCGAAGGTGG AGTT                                           24
```

(2) INFORMATION FOR SEQ ID NO:20:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(ix) FEATURE:
        (A) NAME/KEY: CDS
        (B) LOCATION: 1..346

(xi) SEQUENCE DESCRIPTION: SEQ ID NO:20:

```
ATG CCG ATG TTC ATC GTA AAC ACC AAC GTG CCC CGC GCC TCC GTG CCG      48
Met Pro Met Phe Ile Val Asn Thr Asn Val Pro Arg Ala Ser Val Pro
            120                 125                 130

GAC GGG TTC CTC TCC GAG CTC ACC CAG CAG CTG GCG CAG GCC ACC GGC      96
Asp Gly Phe Leu Ser Glu Leu Thr Gln Gln Leu Ala Gln Ala Thr Gly
            135                 140                 145

AAG CCC CCC CAG TAC ATC GCG GTG CAC GTG GTC CCG GAC CAG CTC ATG     144
Lys Pro Pro Gln Tyr Ile Ala Val His Val Val Pro Asp Gln Leu Met
            150                 155                 160

GCC TTC GGC GGC TCC AGC GAG CCG AGC GCG CTC TGC AGC CTG CAC AGC     192
Ala Phe Gly Gly Ser Ser Glu Pro Ser Ala Leu Cys Ser Leu His Ser
            165                 170                 175

ATC GGC AAG ATC GGC GGC GCG CAG AAC CGC TCC TAC AGC AAG CTG CTG     240
Ile Gly Lys Ile Gly Gly Ala Gln Asn Arg Ser Tyr Ser Lys Leu Leu
180                 185                 190                 195

TGC GGC CTG CTG GCC GAG CGC CTG CGC ATC AGC CCG GAC AGG GTC TAC     288
Cys Gly Leu Leu Ala Glu Arg Leu Arg Ile Ser Pro Asp Arg Val Tyr
                200                 205                 210

ATC AAC TAT TAC GAC ATG AAC GCG GCC AAT GTG GGC TGG AAC AAC TCC     336
Ile Asn Tyr Tyr Asp Met Asn Ala Ala Asn Val Gly Trp Asn Asn Ser
            215                 220                 225

ACC TTC GCC  T AA                                                   348
Thr Phe Ala
        230
```

(2) INFORMATION FOR SEQ ID NO:21:

(i) SEQUENCE CHARACTERISTICS:
        (A) LENGTH:115 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:21:

```
Met Pro Met Phe Ile Val Asn Thr Asn Val Pro Arg Ala Ser Val Pro
 1           5              10               15

Asp Gly Phe Leu Ser Glu Leu Thr Gln Gln Leu Ala Gln Ala Thr Gly
            20              25              30

Lys Pro Pro Gln Tyr Ile Ala Val His Val Val Pro Asp Gln Leu Met
        35              40              45

Ala Phe Gly Gly Ser Ser Glu Pro Cys Ala Leu Cys Ser Leu His Ser
    50              55              60

Ile Gly Lys Ile Gly Gly Ala Gln Asn Arg Ser Tyr Ser Lys Leu Leu
 65              70              75               80

Cys Gly Leu Leu Ala Glu Arg Leu Arg Ile Ser Pro Asp Arg Val Tyr
            85              90              95

Ile Asn Tyr Tyr Asp Met Asn Ala Ala Asn Val Gly Trp Asn Asn Ser
         100             105             110

Thr Phe Ala
        115
```